(12) United States Patent
Rath

(10) Patent No.: US 7,300,918 B2
(45) Date of Patent: Nov. 27, 2007

(54) METHOD OF PRODUCING VACCINES FROM PROTEIN SIGNAL OLIGOPEPTIDES

(76) Inventor: Matthias Rath, Ambachtstraat 20, 7609 Ra Almelo (NL)

( * ) Notice: Subject to any disclaimer, the term of this patent is extended or adjusted under 35 U.S.C. 154(b) by 0 days.

(21) Appl. No.: 10/930,300

(22) Filed: Aug. 30, 2004

(65) Prior Publication Data

US 2005/0014138 A1    Jan. 20, 2005

Related U.S. Application Data

(63) Continuation-in-part of application No. 09/881,976, filed on Jun. 15, 2001, now abandoned, which is a continuation of application No. 09/232,186, filed on Jan. 14, 1999, now abandoned, which is a continuation-in-part of application No. 08/704,499, filed as application No. PCT/US95/00575 on Jan. 12, 1995, now abandoned, which is a continuation of application No. 08/182,248, filed on Jan. 14, 1994, now abandoned.

(51) Int. Cl.
*A01N 37/18* (2006.01)
*A61K 38/00* (2006.01)

(52) U.S. Cl. ........................................ 514/2
(58) Field of Classification Search .............. 435/7.1, 435/7.21; 514/2; 530/300, 308, 324, 350
See application file for complete search history.

(56) References Cited

U.S. PATENT DOCUMENTS 4,554,101 A    11/1985    Hopp

FOREIGN PATENT DOCUMENTS

WO    WO 89/05823    6/1989
WO    WO 89/10405    11/1989

OTHER PUBLICATIONS

Rath, "Cationic-Anionic and Anionic-Cationic Oligopeptides in Apoprotein a and other proteins as Modulators of Protein Action . . . ," Journal of Applied Nutrition (1992) vol. 44, Nos. 3 and 4.

Hopp, TP and Woods, KR, Proc. Natl. Acad. Sci. USA (1981) 78:3824-3828.

Boger, Proceedings of the 1988 Miami Bio/Technology Winter Symposium. 10. Oxford and Washington. IRL Press.

Riffkin et al., "A single amino-acid change between the antigenically different extracellular serine proteases V2 and B2 from Dichelobacter nodosus," Gene, vol. 167 (1995) pp. 279-283.

Abaza et al., "Effects of amino acid substitutions outside an antigenic site on protein binding to monoclonal antibodies of predetermined specificity obtained by peptide immunization," Journal of Protein Chemistry (1992) vol. 11, No. 5, pp. 433-444.

Cruse et al., *Illustrated Dictionary of Immunolgy* (Boca Raton, FL, CRC Press, Inc., 1995) p. 309 QR180.4.C78.

Paul, *Fundamental Immunology* (Philadelphia & New York, Lippincott-Raven Publishers, 1993) pp. 250 and 1311-1312 QR181. F84.

Cohen et al., "Pronounced acute immunosuppression in vivo mediated by HIV Tat challenge," Proceedings of the National Academy of Sciences of the United States of America (Sep. 14, 1999) vol. 96, Issue 19, pp. 10842-10847.

Watanabe et al., "Molecular Cloning of a Novel Ca (2+)-Binding protein (calmegin) Specifically Expressed During Male Meiotic Germ Cell Development," Journal of Biological Chemistry (Mar. 11, 1994) vol. 269, No. 10, pp. 7744-7749.

Hogh et al., "Glutamate Rich Plasmodium Falciparum Antigen (GLURP)," Parassitologia (Jul. 1993) vol. 35, Suppl. 47-50.

*Primary Examiner*—Jeffrey Parkin
*Assistant Examiner*—Louise Humphrey
(74) *Attorney, Agent, or Firm*—Ali Kamarei, Esq.; Alexander Chen, Esq.

(57) ABSTRACT

The description discloses a method of producing therapeutic peptides as vaccines in the prevention of human diseases that are caused by one or more proteins. The method comprises identifying the protein responsible for causing the human disease; identifying one or more signal oligopeptide sequences within the structure of the disease causing protein, the one or more signal oligopeptides representing the amino acid sequence of maximum hydrophilicity; and synthesizing one or more vaccine oligopeptides, the vaccine oligopeptides having amino acid sequences corresponding to the amino acid sequences of the signal oligopeptides of maximum hydrophilicity.

1 Claim, 10 Drawing Sheets

Synthetic Analogs of
Signal Peptides
Competitively Inhibit
Interaction

Anitbodies Against
Signal Peptides
Block Interaction

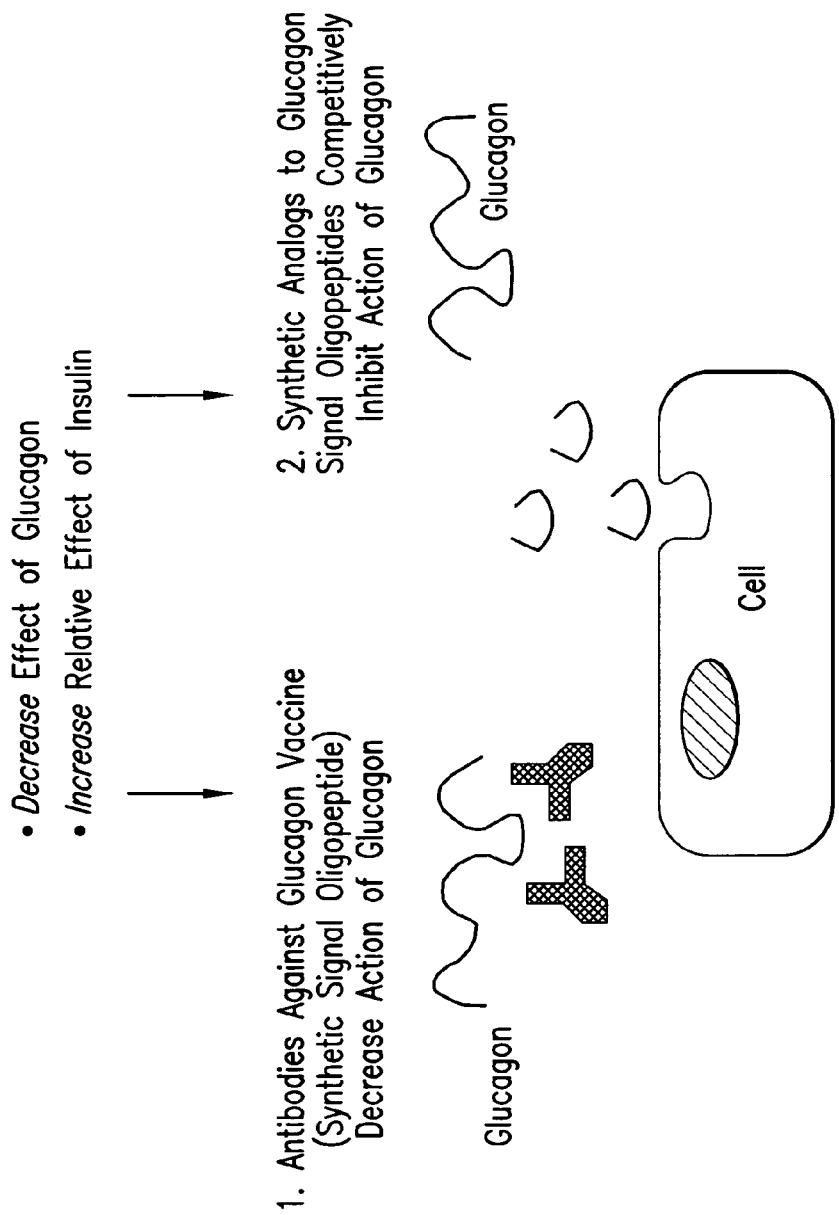

SEQUENCE LISTING (1) GENERAL INFORMATION:

(iii) NUMBER OF SEQUENCES: 360

(2) INFORMATION FOR SEQ ID NO: 1:

(i) SEQUENCE CHARACTERISTICS:
          (A) LENGTH: 9
          (B) TYPE: amino acid
          (C) STRANDEDNESS: single
          (D) TOPOLOGY: linear (xi) SEQUENCE DESCRIPTION: SEQ ID NO: 1:

Asp Val Tyr Ala Gln Glu Lys Gln Asp
1               5

(2) INFORMATION FOR SEQ ID NO: 2:

(i) SEQUENCE CHARACTERISTICS:
          (A) LENGTH: 9
          (B) TYPE: amino acid
          (C) STRANDEDNESS: single
          (D) TOPOLOGY: linear (xi) SEQUENCE DESCRIPTION: SEQ ID NO: 2:

Asp Val His Asn Gln Glu Lys Gln Asn
1               5

(2) INFORMATION FOR SEQ ID NO: 3:

(i) SEQUENCE CHARACTERISTICS:
          (A) LENGTH: 6
          (B) TYPE: amino acid
          (C) STRANDEDNESS: single
          (D) TOPOLOGY: linear (xi) SEQUENCE DESCRIPTION: SEQ ID NO: 3:

Glu Ile Arg Arg Glu Arg
1               5

(2) INFORMATION FOR SEQ ID NO: 4:

(i) SEQUENCE CHARACTERISTICS:
          (A) LENGTH: 11
          (B) TYPE: amino acid
          (C) STRANDEDNESS: single
          (D) TOPOLOGY: linear (xi) SEQUENCE DESCRIPTION: SEQ ID NO: 4:

Glu Asp Glu Met Gly His Pro Glu Ile Gly Asp
1               5                   10

(2) INFORMATION FOR SEQ ID NO: 5:

(i) SEQUENCE CHARACTERISTICS:
          (A) LENGTH: 11
          (B) TYPE: amino acid
          (C) STRANDEDNESS: single
          (D) TOPOLOGY: linear (xi) SEQUENCE DESCRIPTION: SEQ ID NO: 5:

Glu Asp Glu Leu Gly His Pro Glu Lys Gly Asp
1               5                   10

(2) INFORMATION FOR SEQ ID NO: 6:

```
    (i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 6:

Ala Ser Leu Leu Ala Tyr Gly Met Pro Lys Glu
1               5                   10

(2) INFORMATION FOR SEQ ID NO: 7:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 7:

Glu Pro Arg Lys Gln Asp Ala Asp
1               5

(2) INFORMATION FOR SEQ ID NO: 8:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 8:

Glu Pro Arg Lys Gln Asp Ala Glu
1               5

(2) INFORMATION FOR SEQ ID NO: 9:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 9:

Asn Lys Thr Val Glu Gln Leu Gly Gln Glu Glu
1               5                   10

(2) INFORMATION FOR SEQ ID NO: 10:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 10:

Asp Asp Ile Met Asp Ser Ser Leu Thr Arg Arg
1               5                   10

(2) INFORMATION FOR SEQ ID NO: 11:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 11:
```

```
Asp Asp Ile Met Asp Ser Ser Tyr Thr Arg Arg
1               5                   10
```

(2) INFORMATION FOR SEQ ID NO: 12:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 12:

```
Asp Asp Met Met Asp Lys Ser Ile Thr Arg Arg
1               5                   10
```

(2) INFORMATION FOR SEQ ID NO: 13:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 13:

```
Lys Leu Tyr Cys Arg Glu Gln Pro Tyr Tyr
1               5                   10
```

(2) INFORMATION FOR SEQ ID NO: 14:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 14:

```
Lys Ser His Phe Arg Asn Glu Lys Tyr Tyr
1               5                   10
```

(2) INFORMATION FOR SEQ ID NO: 15:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 15:

```
Arg Phe Thr Glu Lys Arg Tyr Lys
1               5
```

(2) INFORMATION FOR SEQ ID NO: 16:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 16:

```
Arg Tyr Thr Glu Lys Arg Tyr Lys
1               5
```

(2) INFORMATION FOR SEQ ID NO: 17:

(i) SEQUENCE CHARACTERISTICS:
        (A) LENGTH: 8
        (B) TYPE: amino acid

```
        (C) STRANDEDNESS: single
        (D) TOPOLOGY: linear (xi) SEQUENCE DESCRIPTION: SEQ ID NO: 17:

Lys Phe Ser Leu Lys Lys His Ser
1               5

(2) INFORMATION FOR SEQ ID NO: 18:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 18:

Lys Val Asp Leu Ser Lys Phe Ser Leu Lys Lys
1               5                   10

(2) INFORMATION FOR SEQ ID NO: 19:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 19:

Lys Lys His Ser Phe Ile Val Thr Phe Lys Thr
1               5                   10

(2) INFORMATION FOR SEQ ID NO: 20:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 20:

Asp Gly Glu Lys Glu His Ala Asn Ala Lys Lys
1               5                   10

(2) INFORMATION FOR SEQ ID NO: 21:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 21:

Asp Gly Glu Lys Glu His Ala Asn Ala Leu Lys
1               5                   10

(2) INFORMATION FOR SEQ ID NO: 22:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 22:

Thr Asp Glu Lys Asp Leu Lys Gln Ala Arg Asp
1               5                   10
```

(2) INFORMATION FOR SEQ ID NO: 23:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 23:

Lys Ile Gly Thr Asp Ile Gln Asp Asn Lys
1               5                   10

(2) INFORMATION FOR SEQ ID NO: 24:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 24:

Lys Val Gly Thr Asp Ile Gln Asp Asn Lys
1               5                   10

(2) INFORMATION FOR SEQ ID NO: 25:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 25:

Gln Arg Ala Thr Pro Glu Gln Tyr
1               5

(2) INFORMATION FOR SEQ ID NO: 26:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 26:

Leu Arg Ala Thr Pro Gln Gln Arg
1               5

(2) INFORMATION FOR SEQ ID NO: 27:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 27:

Glu Leu Ala Ser Ala Glu Gln Arg
1               5

(2) INFORMATION FOR SEQ ID NO: 28:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 28:

Lys Glu Asn Tyr Gly Gln Lys Glu Ala Glu Lys
1               5                   10

(2) INFORMATION FOR SEQ ID NO: 29:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 29:

Glu Glu Asn Tyr Gly Gln Lys Asp Pro Glu Lys
1               5                   10

(2) INFORMATION FOR SEQ ID NO: 30:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 30:

Asp Glu Asn Tyr Gly Lys Lys Asp Ser
1               5

(2) INFORMATION FOR SEQ ID NO: 31:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 31:

Arg Val Lys Ala Leu Tyr Glu Glu Leu
1               5

(2) INFORMATION FOR SEQ ID NO: 32:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 32:

Lys Cys Lys Lys Ile Phe Asn Asp Leu
1               5

(2) INFORMATION FOR SEQ ID NO: 33:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 33:

Lys Glu Ala Glu Lys Val Ala Arg Val Lys
1               5                   10

(2) INFORMATION FOR SEQ ID NO: 34:

(i) SEQUENCE CHARACTERISTICS:
        (A) LENGTH: 10

```
            (B) TYPE: amino acid
            (C) STRANDEDNESS: single
            (D) TOPOLOGY: linear (xi) SEQUENCE DESCRIPTION: SEQ ID NO: 34:

Lys Asp Ser Val Ala Glu Ala Lys Cys Lys
1               5                   10

(2) INFORMATION FOR SEQ ID NO: 35:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 35:

Lys Asp Pro Glu Lys Val Ala Arg
1               5

(2) INFORMATION FOR SEQ ID NO: 36:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 36:

Gln Tyr Glu Glu Asp Ser Tyr Ser His
1               5

(2) INFORMATION FOR SEQ ID NO: 37:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 37:

Lys Tyr Glu Glu Asp Ser Tyr Asn Arg
1               5

(2) INFORMATION FOR SEQ ID NO: 38:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 38:

Glu Tyr Glu Glu Ser Ile Ala Lys Asp
1               5

(2) INFORMATION FOR SEQ ID NO: 39:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 39:

Arg Lys Ile Tyr Lys Arg Arg Lys
1               5
```

(2) INFORMATION FOR SEQ ID NO: 40:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 40:

Asn Lys Ile Tyr Lys Arg Arg Lys
1               5

(2) INFORMATION FOR SEQ ID NO: 41:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 41:

Asn Lys Val Tyr Lys Arg Ser Lys
1               5

(2) INFORMATION FOR SEQ ID NO: 42:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 42:

Ser Gln Asp Glu Val Arg Glu Asn
1               5

(2) INFORMATION FOR SEQ ID NO: 43:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 43:

Thr Gln Asn Glu Val Val Asp Asn
1               5

(2) INFORMATION FOR SEQ ID NO: 44:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 44:

Glu Leu Ser Arg Glu Ser Arg Glu Gly Arg
1               5                   10

(2) INFORMATION FOR SEQ ID NO: 45:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 45:

Glu Leu Ser Asn Ser Asn Lys Tyr Gly Arg
1               5                   10

(2) INFORMATION FOR SEQ ID NO: 46:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 46:

Arg Val Leu Glu Glu Glu Glu Asn Lys
1               5

(2) INFORMATION FOR SEQ ID NO: 47:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 47:

Glu Val Leu Glu Glu Glu Glu Asp Arg Lys
1               5                   10

(2) INFORMATION FOR SEQ ID NO: 48:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 48:

Lys Gly Val Ser Ser Ser Thr Arg Lys
1               5

(2) INFORMATION FOR SEQ ID NO: 49:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 49:

Ser Val Leu Glu Glu Glu Glu Asp Asn Lys
1               5                   10

(2) INFORMATION FOR SEQ ID NO: 50:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 50:

Asp Glu Asn Val Ser Lys Arg Ile Glu Pro
1               5                   10

(2) INFORMATION FOR SEQ ID NO: 51:

(i) SEQUENCE CHARACTERISTICS:

```
        (A) LENGTH: 9
        (B) TYPE: amino acid
        (C) STRANDEDNESS: single
        (D) TOPOLOGY: linear (xi) SEQUENCE DESCRIPTION: SEQ ID NO: 51:

Asp Asp Met Met Pro Lys Arg Val Glu
1               5

(2) INFORMATION FOR SEQ ID NO: 52:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 52:

Asp Pro Thr Met Pro Leu Trp Glu Phe
1               5

(2) INFORMATION FOR SEQ ID NO: 53:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 53:

Lys Lys Val Pro Asp Asn Cys Cys Arg Arg Glu
1               5                   10

(2) INFORMATION FOR SEQ ID NO: 54:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 54:

Lys Lys Ala Pro Asp Asn Cys Cys Arg Arg Glu
1               5                   10

(2) INFORMATION FOR SEQ ID NO: 55:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 55:

Lys Lys Gln Ile Glu Ser Cys Arg Arg Glu
1               5                   10

(2) INFORMATION FOR SEQ ID NO: 56:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 56:

Gln Lys Cys Asp Ser Val Glu Glu
1               5
```

(2) INFORMATION FOR SEQ ID NO: 57:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 57:

```
Glu  Lys  Leu  Ser  Ser  Val  Glu  Glu
1                    5
```

(2) INFORMATION FOR SEQ ID NO: 58:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 58:

```
His  Val  Ser  Thr  Thr  Glu  Glu
1                    5
```

(2) INFORMATION FOR SEQ ID NO: 59:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 59:

```
Glu  Thr  Leu  Ile  Ser  Asp  Gln
1                    5
```

(2) INFORMATION FOR SEQ ID NO: 60:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 60:

```
Glu  Glu  Thr  Gly  Ile  Asn  Arg  Glu  Arg  Lys  Val  Glu
1                    5                        10
```

(2) INFORMATION FOR SEQ ID NO: 61:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 61:

```
Glu  Glu  Pro  Gly  Val  Ser  Gln  Asp  Arg  Lys  Val  Glu
1                    5                        10
```

(2) INFORMATION FOR SEQ ID NO: 62:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 62:

Glu Ala Ser Ser Lys Glu Glu Thr Glu Ala
1               5                   10

(2) INFORMATION FOR SEQ ID NO: 63:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 63:

Thr Asp Pro Val Thr Ala Ser Pro Arg Asn
1               5                   10

(2) INFORMATION FOR SEQ ID NO: 64:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 64:

Glu Pro Glu Ile Glu Leu Pro Arg Glu Pro Arg Pro
1               5                   10

Asn Glu Glu
        15

(2) INFORMATION FOR SEQ ID NO: 65:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 65:

Glu Leu Glu Ile Glu Leu Pro Ser Glu Pro Arg Pro
1               5                   10

Asn Glu Glu
        15

(2) INFORMATION FOR SEQ ID NO: 66:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 66:

Asn Thr Met Phe Asp Leu Pro Glu Glu Pro Arg Pro
1               5                   10

Leu Asp Glu
        15

(2) INFORMATION FOR SEQ ID NO: 67:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 67:

Glu Val Glu Trp Val Leu Glu Thr Glu Leu Lys Ala
1               5                   10
Pro Arg Pro
        15

(2) INFORMATION FOR SEQ ID NO: 68:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 68:

Arg Glu Pro Arg Pro Asn Glu Glu Cys
1               5

(2) INFORMATION FOR SEQ ID NO: 69:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 69:

Glu Leu Lys Ala Pro Arg Pro Met
1               5

(2) INFORMATION FOR SEQ ID NO: 70:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 70:

Glu Glu Pro Arg Pro Leu Asp Glu Cys
1               5

(2) INFORMATION FOR SEQ ID NO: 71:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 71:

His Glu Arg Gly Val Ser Ile Arg Arg Gln Leu Leu
1               5                   10
Ser Lys Lys
        15

(2) INFORMATION FOR SEQ ID NO: 72:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 72:

```
Pro Arg Glu Gly Val Ala Ile Arg Arg Gln Met Leu
1               5                   10

Ser Asp Lys
        15
```

(2) INFORMATION FOR SEQ ID NO: 73:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 73:

```
Pro Glu Arg Gly Val Ala Val Arg Arg Gln Ile Ile
1               5                   10

Ser Lys
```

(2) INFORMATION FOR SEQ ID NO: 74:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 74:

```
Pro Phe Arg Ala Val Glu Leu Arg Arg Leu Asp Leu
1               5                   10
```

(2) INFORMATION FOR SEQ ID NO: 75:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 75:

```
Leu Gln Tyr Leu Pro Tyr Arg Asp Tyr Asn
1               5                   10
```

(2) INFORMATION FOR SEQ ID NO: 76:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 76:

```
Ile Glu Arg Ile Pro Tyr Lys Asp Tyr Asp
1               5                   10
```

(2) INFORMATION FOR SEQ ID NO: 77:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 77:

```
Leu Gln Ser Leu Pro Tyr Lys Asn Tyr Asn
1               5                   10
```

-continued (2) INFORMATION FOR SEQ ID NO: 78:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 78:

Leu Glu Lys Leu Pro Tyr Ala Ser Tyr Asp
1               5                   10

(2) INFORMATION FOR SEQ ID NO: 79:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 79:

Cys Leu Asp Glu Lys Glu Phe Gln
1               5

(2) INFORMATION FOR SEQ ID NO: 80:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 80:

Cys Leu Asp Gly Lys Glu Tyr Gln
1               5

(2) INFORMATION FOR SEQ ID NO: 81:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 81:

Leu Leu Asn Asn Lys Glu Tyr Gln
1               5

(2) INFORMATION FOR SEQ ID NO: 82:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 82:

Leu Leu Asp Gly Gln Glu Phe Gln
1               5

(2) INFORMATION FOR SEQ ID NO: 83:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 83:

```
Leu Leu Asp Gly Arg Ser His Tyr
1               5
```

(2) INFORMATION FOR SEQ ID NO: 84:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 84:

```
Arg Leu Pro Arg Ala Cys Asp Ser Ala Glu Val Lys
1               5                   10
```

(2) INFORMATION FOR SEQ ID NO: 85:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 85:

```
Arg Leu Pro Thr Ala Cys Asp Ala Ala Glu Val Lys
1               5                   10
```

(2) INFORMATION FOR SEQ ID NO: 86:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 86:

```
Arg Leu Pro Ser Ala Gln Glu Ala Gly Ala Ile Lys
1               5                   10
```

(2) INFORMATION FOR SEQ ID NO: 87:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 87:

```
Glu Lys Ala Leu Ser Lys Leu His Glu Tyr
1               5                   10
```

(2) INFORMATION FOR SEQ ID NO: 88:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 88:

```
Glu Lys Ala Leu Val Lys Leu Gln Glu Phe
1               5                   10
```

(2) INFORMATION FOR SEQ ID NO: 89:

(i) SEQUENCE CHARACTERISTICS:
        (A) LENGTH: 10

(B) TYPE: amino acid
        (C) STRANDEDNESS: single
        (D) TOPOLOGY: linear (xi) SEQUENCE DESCRIPTION: SEQ ID NO: 89:

Glu Gln Ala Leu Ala Arg Leu Gln Glu Glu
1               5                   10

(2) INFORMATION FOR SEQ ID NO: 90:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 90:

Glu Gln Ala Leu His Ala Leu Gln Thr Met
1               5                   10

(2) INFORMATION FOR SEQ ID NO: 91:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 91:

Cys Lys Asp Asn Pro Gly Glu Asn Ala Arg
1               5                   10

(2) INFORMATION FOR SEQ ID NO: 92:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 92:

Ser Thr Glu Thr Pro Gly Lys Asn Ala Cys
1               5                   10

(2) INFORMATION FOR SEQ ID NO: 93:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 93:

Asn Ile His Gly Ser Gly Leu Asn Ala Ser
1               5                   10

(2) INFORMATION FOR SEQ ID NO: 94:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 94:

His Asn Arg Ser Lys Ile Asn Leu Gln Asp
1               5                   10

(2) INFORMATION FOR SEQ ID NO: 95:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 95:

```
His  Asn  Arg  Ser  Ala  Leu  Asn  Ile  Asp  Glu
1                  5                        10
```

(2) INFORMATION FOR SEQ ID NO: 96:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 96:

```
Asp  Tyr  Ser  Lys  Tyr  Leu  Asp  Ser
1                  5
```

(2) INFORMATION FOR SEQ ID NO: 97:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 97:

```
Asp  Ser  Arg  Arg  Ala  Gln  Asp
1                  5
```

(2) INFORMATION FOR SEQ ID NO: 98:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 98:

```
Asp  Tyr  Ser  Lys  Tyr  Leu  Asp  Ser  Arg  Arg  Ala  Gln
1                  5                        10
Asp
```

(2) INFORMATION FOR SEQ ID NO: 99:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 99:

```
Asp  Val  Ala  Ser  Leu  Thr  Asp  Tyr  Leu  Lys  Ser  Lys
1                  5                        10
Arg
```

(2) INFORMATION FOR SEQ ID NO: 100:

(i) SEQUENCE CHARACTERISTICS:
        (A) LENGTH: 13

(B) TYPE: amino acid
        (C) STRANDEDNESS: single
        (D) TOPOLOGY: linear (xi) SEQUENCE DESCRIPTION: SEQ ID NO: 100:

Asp Tyr Ser Lys Tyr Met Asp Asn Arg Arg Ala Lys
1               5                   10

Asp (2) INFORMATION FOR SEQ ID NO: 101:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 101:

Asp Tyr Ser Lys Tyr Leu Asp Asn Arg Arg Ala Lys
1               5                   10

Asp (2) INFORMATION FOR SEQ ID NO: 102:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 102:

Asp Tyr Ser Lys Tyr Leu Asp Ser Arg Arg Ala Gln
1               5                   10

Gln (2) INFORMATION FOR SEQ ID NO: 103:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 103:

Asp Tyr Ser Lys Tyr Leu Asp Ser
1               5

(2) INFORMATION FOR SEQ ID NO: 104:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 104:

Asp Ser Arg Arg Ala Gln Asp
1               5

(2) INFORMATION FOR SEQ ID NO: 105:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 105:

Asp Tyr Ser Lys Tyr Leu Asp Ser Arg Arg Ala Gln
1               5                   10
Asp (2) INFORMATION FOR SEQ ID NO: 106:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 106:

Asp Val Ala Ser Leu Thr Asp Tyr Leu Lys Ser Lys
1               5                   10
Arg (2) INFORMATION FOR SEQ ID NO: 107:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 107:

Asp Tyr Ser Lys Tyr Met Asp Asn Arg Arg Ala Lys
1               5                   10
Asp (2) INFORMATION FOR SEQ ID NO: 108:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 108:

Asp Tyr Ser Lys Tyr Leu Asp Asn Arg Arg Ala Lys
1               5                   10
Asp (2) INFORMATION FOR SEQ ID NO: 109:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 109:

Asp Tyr Ser Lys Tyr Leu Asp Ser Arg Arg Ala Gln
1               5                   10
Gln (2) INFORMATION FOR SEQ ID NO: 110:

(i) SEQUENCE CHARACTERISTICS:
        (A) LENGTH: 13
        (B) TYPE: amino acid
        (C) STRANDEDNESS: single (D) TOPOLOGY: linear (xi) SEQUENCE DESCRIPTION: SEQ ID NO: 110:

Asp Tyr Ser Lys Phe Leu Asp Thr Arg Arg Ala Gln
1               5                   10
Asp (2) INFORMATION FOR SEQ ID NO: 111:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 111:

Asp Tyr Ser Lys Tyr Gln Glu Glu Arg Met Ala Gln
1               5                   10
Asp (2) INFORMATION FOR SEQ ID NO: 112:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 112:

Asp Tyr Ser Lys Tyr Leu Glu Thr Arg Arg Ala Gln
1               5                   10
Asp (2) INFORMATION FOR SEQ ID NO: 113:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 113:

Asp Tyr Ser Lys Tyr Leu Asp Asn Arg Arg Thr Lys
1               5                   10
Asp (2) INFORMATION FOR SEQ ID NO: 114:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 114:

Asp Met Ser Ser Tyr Leu Glu Glu Lys Ala Ala Lys
1               5                   10
Glu (2) INFORMATION FOR SEQ ID NO: 115:

(i) SEQUENCE CHARACTERISTICS:
        (A) LENGTH: 13
        (B) TYPE: amino acid

```
            (C) STRANDEDNESS: single
            (D) TOPOLOGY: linear (xi) SEQUENCE DESCRIPTION: SEQ ID NO: 115:

Asp  Phe  Asn  Lys  Ala  Leu  Asp  Ile  Lys  Ala  Ala  Gln
1                   5                        10

Glu (2) INFORMATION FOR SEQ ID NO: 116:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 116:

Asp  Pro  Leu  Ser  Asp  Pro  Asp  Gln  Met
1                   5

(2) INFORMATION FOR SEQ ID NO: 117:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 117:

Asn  Glu  Asp  Lys  Arg  His  Ser  Gln
1                   5

(2) INFORMATION FOR SEQ ID NO: 118:

(i) SEQUENCE CHARACTERISTICS:
            (A) LENGTH: 15
            (B) TYPE: amino acid
            (C) STRANDEDNESS: single
            (D) TOPOLOGY: linear (xi) SEQUENCE DESCRIPTION: SEQ ID NO: 118:

Lys  Asp  Glu  Pro  Arg  Glu  Leu  Ser  Asn  Met  Lys  Arg
1                   5                        10

His  Ser  Glu
           15

(2) INFORMATION FOR SEQ ID NO: 119:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 119:

Arg  Glu  Leu  Ser  Asn  Met  Lys  Arg  His
1                   5

(2) INFORMATION FOR SEQ ID NO: 120:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 120:
```

```
Glu Ala Arg Glu Leu Ser Thr Pro Lys Xaa His Ser
1               5                   10

Glu
```

(2) INFORMATION FOR SEQ ID NO: 121:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 121:

```
Glu Asp Pro Asp Gln Ile Asn Glu Asp Lys Arg His
1               5                   10
```

(2) INFORMATION FOR SEQ ID NO: 122:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 122:

```
Asp Asp Pro Asp Gln Met Asn Glu Asp Lys Arg His
1               5                   10

Ser Gln
```

(2) INFORMATION FOR SEQ ID NO: 123:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 123:

```
Gly Asp Pro Asp Gln Ile Asn Glu Asp Lys Arg His
1               5                   10

Ser Gln
```

(2) INFORMATION FOR SEQ ID NO: 124:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 124:

```
Asp Glu Ser Arg Gln Leu Asn Glu Val Lys Arg His
1               5                   10

Ser Gln
```

(2) INFORMATION FOR SEQ ID NO: 125:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 125:

```
Met Asn Thr Lys Arg Asn Arg Asn Asn
1               5
```

(2) INFORMATION FOR SEQ ID NO: 126:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 126:

```
Lys Arg His Asp Glu Phe Glu Arg His
1               5
```

(2) INFORMATION FOR SEQ ID NO: 127:

(i) SEQUENCE CHARACTERISTICS:
        (A) LENGTH: 20
        (B) TYPE: amino acid
        (C) STRANDEDNESS: single
        (D) TOPOLOGY: linear (xi) SEQUENCE DESCRIPTION: SEQ ID NO: 127:

```
Met Asn Thr Lys Arg Asn Arg Asn Arg Asn Asn Lys
1               5                   10
Arg His Asp Glu Phe Glu Arg His
                15                  20
```

(2) INFORMATION FOR SEQ ID NO: 128:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 128:

```
Asn Lys Arg Ser Gly Val Ala Glu Lys Arg
1               5                   10
```

(2) INFORMATION FOR SEQ ID NO: 129:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 129:

```
Val Lys Arg Asn Arg Asn Asn Ile Ala Lys Arg
1               5                   10
```

(2) INFORMATION FOR SEQ ID NO: 130:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 130:

```
Lys Asn Thr Lys Arg Asn Arg Asn Glu
1               5
```

(2) INFORMATION FOR SEQ ID NO: 131:

```
        (i) SEQUENCE CHARACTERISTICS:
            (A) LENGTH: 12
            (B) TYPE: amino acid
            (C) STRANDEDNESS: single
            (D) TOPOLOGY: linear (xi) SEQUENCE DESCRIPTION: SEQ ID NO: 131:

Thr Lys Arg Asn Gly Xaa Xaa Gly Gln Glu Asp Lys
1               5                   10

(2) INFORMATION FOR SEQ ID NO: 132:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 132:

Gln Glu Asp Lys Glu Asn Asp Lys Phe
1               5

(2) INFORMATION FOR SEQ ID NO: 133:

(i) SEQUENCE CHARACTERISTICS:
            (A) LENGTH: 11
            (B) TYPE: amino acid
            (C) STRANDEDNESS: single
            (D) TOPOLOGY: linear (xi) SEQUENCE DESCRIPTION: SEQ ID NO: 133:

Lys Arg His Ser Glu Phe Glu Arg His Ala Glu
1               5                   10

(2) INFORMATION FOR SEQ ID NO: 134:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 134:

Gln Asp Thr Glu Glu Lys Ser Arg
1               5

(2) INFORMATION FOR SEQ ID NO: 135:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 135:

Gln Asp Thr Glu Glu Lys Pro Arg
1               5

(2) INFORMATION FOR SEQ ID NO: 136:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 136:

Gln Asp Thr Glu Glu Asn Ala Arg
```

```
1               5
```

(2) INFORMATION FOR SEQ ID NO: 137:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 137:

```
Asp Gln Asp Pro Asp Arg Asn Ser Met
1               5
```

(2) INFORMATION FOR SEQ ID NO: 138:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 138:

```
Lys Gly Arg Gly Arg Arg Asp Phe Pro Glu Glu
1               5                   10
```

(2) INFORMATION FOR SEQ ID NO: 139:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 139:

```
Asp Arg Leu Lys Ala Gln Val Arg Arg Glu
1               5                   10
```

(2) INFORMATION FOR SEQ ID NO: 140:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 140:

```
Ala Lys Leu Lys Ser Gly Lys Val
1               5
```

(2) INFORMATION FOR SEQ ID NO: 141:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 141:

```
Lys Ser Gly Gln Pro Lys Pro Glu
1               5
```

(2) INFORMATION FOR SEQ ID NO: 142:

(i) SEQUENCE CHARACTERISTICS:
        (A) LENGTH: 8
        (B) TYPE: amino acid
        (C) STRANDEDNESS: single (D) TOPOLOGY: linear (xi) SEQUENCE DESCRIPTION: SEQ ID NO: 142:

Lys Gln Gly Gln Asp Arg Arg Glu
1               5

(2) INFORMATION FOR SEQ ID NO: 143:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 143:

Ala Asp Pro Ser Lys Lys Gln
1               5

(2) INFORMATION FOR SEQ ID NO: 144:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 144:

Arg Thr Asp Leu Ser Lys Lys Gln
1               5

(2) INFORMATION FOR SEQ ID NO: 145:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 145:

Ala Asp Leu Ser Lys Lys Gln
1               5

(2) INFORMATION FOR SEQ ID NO: 146:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 146:

Asp Leu Ser Lys Lys Gln Arg
1               5

(2) INFORMATION FOR SEQ ID NO: 147:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 147:

Trp Leu Glu Glu Glu Glu Glu Ala
1               5

(2) INFORMATION FOR SEQ ID NO: 148:

```
        (i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 148:

Trp Met Glu Glu Glu Glu Ala
1               5

(2) INFORMATION FOR SEQ ID NO: 149:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 149:

Trp Val Glu Glu Glu Glu Ala
1               5

(2) INFORMATION FOR SEQ ID NO: 150:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 150:

Trp Ala Glu Glu Glu Glu Ala
1               5

(2) INFORMATION FOR SEQ ID NO: 151:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 151:

Pro Met Glu Glu Glu Glu Glu Ala
1               5

(2) INFORMATION FOR SEQ ID NO: 152:

(i) SEQUENCE CHARACTERISTICS:
            (A) LENGTH: 11
            (B) TYPE: amino acid
            (C) STRANDEDNESS: single
            (D) TOPOLOGY: linear (xi) SEQUENCE DESCRIPTION: SEQ ID NO: 152:

Asp Phe Gly Arg Arg Ser Ala Glu Asp Glu Asn
1               5                   10

(2) INFORMATION FOR SEQ ID NO: 153:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 153:
```

```
Met Asp Phe Gly Arg Arg Ser
1               5
```

(2) INFORMATION FOR SEQ ID NO: 154:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 154:

```
Arg Arg Ser Ala Glu Asp Glu
1               5
```

(2) INFORMATION FOR SEQ ID NO: 155:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 155:

```
Arg Arg Ser Ala Glu Asp Gly Asp Gln His Pro
1               5                   10
```

(2) INFORMATION FOR SEQ ID NO: 156:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 156:

```
Arg Asp Leu Glu Leu Pro Trp Leu Glu
1               5
```

(2) INFORMATION FOR SEQ ID NO: 157:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 157:

```
Arg Gly Lys Glu Pro His Glu Leu Asp Arg
1               5                   10
```

(2) INFORMATION FOR SEQ ID NO: 158:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 158:

```
Arg Gly Gln Glu Pro Leu Arg
1               5
```

(2) INFORMATION FOR SEQ ID NO: 159:

(i) SEQUENCE CHARACTERISTICS:
        (A) LENGTH: 7
        (B) TYPE: amino acid

```
            (C) STRANDEDNESS: single
            (D) TOPOLOGY: linear (xi) SEQUENCE DESCRIPTION: SEQ ID NO: 159:

Glu Pro His Trp Leu Asn Arg
1               5

(2) INFORMATION FOR SEQ ID NO: 160:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 160:

Lys Pro Arg Ser Gln Gln Pro Asp
1               5

(2) INFORMATION FOR SEQ ID NO: 161:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 161:

Lys Pro Gly Phe Gln Leu Gln Asp
1               5

(2) INFORMATION FOR SEQ ID NO: 162:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 162:

Lys Pro His Ser His Leu Gln Asp
1               5

(2) INFORMATION FOR SEQ ID NO: 163:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 163:

Lys Pro Arg Ser Gln Leu Gln Asp
1               5

(2) INFORMATION FOR SEQ ID NO: 164:

(i) SEQUENCE CHARACTERISTICS:
            (A) LENGTH: 12
            (B) TYPE: amino acid
            (C) STRANDEDNESS: single
            (D) TOPOLOGY: linear (xi) SEQUENCE DESCRIPTION: SEQ ID NO: 164:

Gln His Trp Ser Tyr Gly Leu Arg Pro Gly Gly Lys
1               5                   10
```

```
(2) INFORMATION FOR SEQ ID NO: 165:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 165:

Gly Leu Gln Pro Gly Gly Lys Arg Asp
1               5

(2) INFORMATION FOR SEQ ID NO: 166:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 166:

His Gly Trp Leu Pro Gly Gly Lys Arg Asp
1               5                   10

(2) INFORMATION FOR SEQ ID NO: 167:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 167:

Gly Trp Leu Pro Gly Gly Lys Arg Asp
1               5

(2) INFORMATION FOR SEQ ID NO: 168:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 168:

His Gly Trp Tyr Pro Gly Gly Lys Arg Asp
1               5                   10

(2) INFORMATION FOR SEQ ID NO: 169:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 169:

Gln His Tyr Ser Leu Glu Trp Lys Pro Gly
1               5                   10

(2) INFORMATION FOR SEQ ID NO: 170:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 170:
```

Arg Pro Gly Gly Lys Arg Asp Ala Glu
1               5

(2) INFORMATION FOR SEQ ID NO: 171:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 171:

Arg Pro Gly Gly Lys Arg Asn Thr Glu His
1               5                   10

(2) INFORMATION FOR SEQ ID NO: 172:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 172:

Gln Pro Gly Gly Lys Arg Asp Ala Glu
1               5

(2) INFORMATION FOR SEQ ID NO: 173:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 173:

Gln Ala Ser Lys Asp Arg
1               5

(2) INFORMATION FOR SEQ ID NO: 174:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 174:

Lys Ile Asp Asp Lys Gly
1               5

(2) INFORMATION FOR SEQ ID NO: 175:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO: 175:

Trp Asn Lys Asp Glu
1               5

(2) INFORMATION FOR SEQ ID NO: 176:

(i) SEQUENCE CHARACTERISTICS:
        (A) LENGTH: 6

```
        (B) TYPE: amino acid
        (C) STRANDEDNESS: single
        (D) TOPOLOGY: linear (xi) SEQUENCE DESCRIPTION: SEQ ID NO: 176:

Glu  Val  Glu  Arg  Ala  Arg
1                    5

(2) INFORMATION FOR SEQ ID NO: 177:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 177:

His  Arg  Arg  Leu  Phe  His  Lys  Ser  Asp
1                    5

(2) INFORMATION FOR SEQ ID NO: 178:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 178:

Lys  Thr  Pro  Phe  Pro  Asp  Ser
1                    5

(2) INFORMATION FOR SEQ ID NO: 179:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 179:

Tyr  Glu  Lys  Glu  Val  Pro
1                    5

(2) INFORMATION FOR SEQ ID NO: 180:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 180:

Glu  Val  Asp  Leu  Arg  Lys  Pro
1                    5

(2) INFORMATION FOR SEQ ID NO: 181:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 181:

Lys  Val  Lys  Ile  Glu  Val  Asn  Glu
1                    5
```

(2) INFORMATION FOR SEQ ID NO: 182:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 182:

```
Ala  Arg  Met  Ala  Pro  Glu  Glu
1                   5
```

(2) INFORMATION FOR SEQ ID NO: 183:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 183:

```
Arg  Ala  Ser  Lys  Asp  Arg
1                   5
```

(2) INFORMATION FOR SEQ ID NO: 184:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 184:

```
Lys  Ile  Glu  Glu  Lys  Gly
1                   5
```

(2) INFORMATION FOR SEQ ID NO: 185:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 185:

```
Lys  Val  Asn  Glu  Lys  Gly
1                   5
```

(2) INFORMATION FOR SEQ ID NO: 186:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 186:

```
Asn  Ile  Ser  Glu  Arg  Gly
1                   5
```

(2) INFORMATION FOR SEQ ID NO: 187:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO: 187:

Trp  Asn  Lys  Asn  Glu
1                    5

(2) INFORMATION FOR SEQ ID NO: 188:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 188:

Lys  Met  Pro  Phe  Pro  Glu  Ser
1                    5

(2) INFORMATION FOR SEQ ID NO: 189:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 189:

Lys  Thr  Pro  Phe  Leu  Glu  Ala
1                    5

(2) INFORMATION FOR SEQ ID NO: 190:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 190:

His  His  Arg  Leu  Phe  His  Lys  Ser  Asp
1                    5

(2) INFORMATION FOR SEQ ID NO: 191:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 191:

His  Gln  Arg  Leu  Phe  His  Lys  Ser  Asp
1                    5

(2) INFORMATION FOR SEQ ID NO: 192:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 192:

Glu  Val  Asp  Leu  Arg  Gly  Pro  Leu  Glu  Lys
1                    5                        10

(2) INFORMATION FOR SEQ ID NO: 193:

(i) SEQUENCE CHARACTERISTICS:

```
        (A) LENGTH: 9
        (B) TYPE: amino acid
        (C) STRANDEDNESS: single
        (D) TOPOLOGY: linear (xi) SEQUENCE DESCRIPTION: SEQ ID NO: 193:

Glu Ile Asp Leu Arg Arg Pro Leu Glu
1               5

(2) INFORMATION FOR SEQ ID NO: 194:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 194:

Ala Arg Met Ala Pro Thr Glu Met
1               5

(2) INFORMATION FOR SEQ ID NO: 195:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 195:

Lys Trp Lys Thr Pro Phe Glu Lys
1               5

(2) INFORMATION FOR SEQ ID NO: 196:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 196:

Arg Glu Lys Leu Asn Ile Gly Tyr Ile Glu Asp Leu
1               5                   10
Lys (2) INFORMATION FOR SEQ ID NO: 197:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 197:

His Ala Lys Leu Asn Ile Gly Tyr Ile Lys Asp Leu
1               5                   10
Lys (2) INFORMATION FOR SEQ ID NO: 198:

(i) SEQUENCE CHARACTERISTICS:
        (A) LENGTH: 10
        (B) TYPE: amino acid
        (C) STRANDEDNESS: single
        (D) TOPOLOGY: linear
```

(xi) SEQUENCE DESCRIPTION: SEQ ID NO: 198:

Lys Asp Lys Met Ala Glu Asp Glu Val Glu
1               5                   10

(2) INFORMATION FOR SEQ ID NO: 199:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 199:

Lys Asp Thr Leu Asp Glu Asp Asp
1               5

(2) INFORMATION FOR SEQ ID NO: 200:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 200:

Lys Leu Glu Glu His Tyr Glu Leu Arg
1               5

(2) INFORMATION FOR SEQ ID NO: 201:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 201:

Lys Leu Ala Gln Ser Tyr Gly Leu Lys
1               5

(2) INFORMATION FOR SEQ ID NO: 202:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 202:

Glu Arg Asn Asp Leu Phe Leu Ser Glu
1               5

(2) INFORMATION FOR SEQ ID NO: 203:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 203:

Asp Val Asn Glu Glu Gly Thr Glu
1               5

(2) INFORMATION FOR SEQ ID NO: 204:

(i) SEQUENCE CHARACTERISTICS:

```
        (A) LENGTH: 8
        (B) TYPE: amino acid
        (C) STRANDEDNESS: single
        (D) TOPOLOGY: linear (xi) SEQUENCE DESCRIPTION: SEQ ID NO: 204:

Asp Val Thr Glu Glu Gly Thr Val
1               5

(2) INFORMATION FOR SEQ ID NO: 205:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 205:

Arg Gly Ser Thr Glu Asp Glu Gln
1               5

(2) INFORMATION FOR SEQ ID NO: 206:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 206:

Gly Gly Asn Thr Glu Gln Gln
1               5

(2) INFORMATION FOR SEQ ID NO: 207:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 207:

Glu Lys Ser Ala Ser Phe Arg Glu Glu
1               5

(2) INFORMATION FOR SEQ ID NO: 208:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 208:

Glu Lys Ser Ala Arg Phe Lys Glu Glu
1               5

(2) INFORMATION FOR SEQ ID NO: 209:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 209:

Glu Glu Ala Arg Lys Lys
1               5
```

(2) INFORMATION FOR SEQ ID NO: 210:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 210:

Glu Glu Ala Arg Glu Lys
1               5

(2) INFORMATION FOR SEQ ID NO: 211:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 211:

Lys Thr Gln Thr Lys Gly Lys
1               5

(2) INFORMATION FOR SEQ ID NO: 212:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 212:

Lys Thr Gln Thr Lys Gly Glu
1               5

(2) INFORMATION FOR SEQ ID NO: 213:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 213:

Glu Gly Ser Val Asp Gly Asp Thr Arg
1               5

(2) INFORMATION FOR SEQ ID NO: 214:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 214:

Glu Gly Ser Val Asp Glu Asp Thr Lys
1               5

(2) INFORMATION FOR SEQ ID NO: 215:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 215:

Asp Ser Ala Asp Ala Glu Glu Asp Asp
1               5

(2) INFORMATION FOR SEQ ID NO: 216:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 216:

Glu Glu Glu Glu Val Ala Glu Val Glu
1               5

(2) INFORMATION FOR SEQ ID NO: 217:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 217:

Glu Glu Glu Glu Ala Asp Asp Asp
1               5

(2) INFORMATION FOR SEQ ID NO: 218:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 218:

Ala Asp Asp Asp Glu Asp Glu Glu Asp Gly
1               5                   10

(2) INFORMATION FOR SEQ ID NO: 219:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 219:

Asp Glu Asp Gly Asp Glu Val Glu
1               5

(2) INFORMATION FOR SEQ ID NO: 220:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 220:

Glu Glu Ala Glu Glu Pro Tyr Glu Glu
1               5

(2) INFORMATION FOR SEQ ID NO: 221:

(i) SEQUENCE CHARACTERISTICS:
            (A) LENGTH: 15
            (B) TYPE: amino acid
            (C) STRANDEDNESS: single
            (D) TOPOLOGY: linear (xi) SEQUENCE DESCRIPTION: SEQ ID NO: 221:

Ala  Asp  Val  Glu  Glu  Glu  Glu  Ala  Asp  Asp  Asp  Glu
1                   5                        10

Asp  Val  Glu
          15

(2) INFORMATION FOR SEQ ID NO: 222:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 222:

Lys  Ala  Lys  Glu  Arg  Leu  Glu
1                   5

(2) INFORMATION FOR SEQ ID NO: 223:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 223:

Glu  Ala  Lys  His  Arg  Glu  Arg
1                   5

(2) INFORMATION FOR SEQ ID NO: 224:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 224:

Arg  Glu  Trp  Glu  Glu  Ala  Glu  Arg
1                   5

(2) INFORMATION FOR SEQ ID NO: 225:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 225:

Arg  Ala  Glu  Gln  Lys  Asp  Arg
1                   5

(2) INFORMATION FOR SEQ ID NO: 226:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 226:

Glu Pro Glu Thr Glu Pro Asp Val Arg
1               5

(2) INFORMATION FOR SEQ ID NO: 227:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 227:

Glu Gly Glu Pro Glu Val Thr Asp
1               5

(2) INFORMATION FOR SEQ ID NO: 228:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 228:

Glu Thr Glu Pro Glu Pro Glu Leu Arg
1               5

(2) INFORMATION FOR SEQ ID NO: 229:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 229:

Glu Asp Val Cys Gly Arg
1               5

(2) INFORMATION FOR SEQ ID NO: 230:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 230:

Glu Asp Val Arg Gly Arg
1               5

(2) INFORMATION FOR SEQ ID NO: 231:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 231:

Glu Asp Leu Arg Asn Arg
1               5

(2) INFORMATION FOR SEQ ID NO: 232:

(i) SEQUENCE CHARACTERISTICS:

```
        (A) LENGTH: 8
        (B) TYPE: amino acid
        (C) STRANDEDNESS: single
        (D) TOPOLOGY: linear (xi) SEQUENCE DESCRIPTION: SEQ ID NO: 232:

His Leu Arg Lys Leu Arg Lys Arg
1               5

(2) INFORMATION FOR SEQ ID NO: 233:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 233:

His Pro Arg Lys Met Lys Arg Arg
1               5

(2) INFORMATION FOR SEQ ID NO: 234:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 234:

His Leu Arg Lys Met Arg Lys Arg
1               5

(2) INFORMATION FOR SEQ ID NO: 235:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 235:

Arg Asp Arg Leu Asp Glu Val Lys Glu
1               5

(2) INFORMATION FOR SEQ ID NO: 236:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 236:

Arg Ala Arg Met Glu Glu
1               5

(2) INFORMATION FOR SEQ ID NO: 237:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 237:

Arg Gly Arg Met Glu Glu
1               5
```

(2) INFORMATION FOR SEQ ID NO: 238:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 238:

Arg Gly Arg Leu Glu Glu
1               5

(2) INFORMATION FOR SEQ ID NO: 239:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 239:

Asp Tyr Thr Glu Val Gln Arg Arg Asn Gln Leu His
1               5                   10
Asp (2) INFORMATION FOR SEQ ID NO: 240:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 240:

Lys Glu Leu Lys Asn Pro Thr Asn Pro Asp
1               5                   10

(2) INFORMATION FOR SEQ ID NO: 241:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 241:

Glu Gly Glu Glu Gly Gly Asp Phe Asp Glu Ala Lys
1               5                   10

(2) INFORMATION FOR SEQ ID NO: 242:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 242:

Asp Glu Ala Lys Leu Ala Glu Ala Arg Glu Met Ile
1               5                   10
Arg (2) INFORMATION FOR SEQ ID NO: 243:

(i) SEQUENCE CHARACTERISTICS:

```
            (A) LENGTH: 9
            (B) TYPE: amino acid
            (C) STRANDEDNESS: single
            (D) TOPOLOGY: linear (xi) SEQUENCE DESCRIPTION: SEQ ID NO: 243:

Asp Met Val Met Arg Lys Arg Arg Asn
1               5

(2) INFORMATION FOR SEQ ID NO: 244:

(i) SEQUENCE CHARACTERISTICS:
            (A) LENGTH: 21
            (B) TYPE: amino acid
            (C) STRANDEDNESS: single
            (D) TOPOLOGY: linear (xi) SEQUENCE DESCRIPTION: SEQ ID NO: 244:

Arg Lys Arg Arg Asn Thr Asn Tyr Thr Gln Val Pro
1               5                   10

Asn Lys Asp Ala Asp Glu Asp Leu
            15              20

(2) INFORMATION FOR SEQ ID NO: 245:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 245:

Lys Ala Arg Lys Arg Lys Thr Lys Lys
1               5

(2) INFORMATION FOR SEQ ID NO: 246:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 246:

Lys Lys Pro Pro Lys Arg Pro Glu
1               5

(2) INFORMATION FOR SEQ ID NO: 247:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 247:

Arg Asp Ala Arg Glu Ala Ile Asp Arg
1               5

(2) INFORMATION FOR SEQ ID NO: 248:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 248:
```

Arg Glu Tyr Met Arg Glu Gln Asp Arg Lys
1               5                   10

(2) INFORMATION FOR SEQ ID NO: 249:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 249:

Arg Lys Arg Asn Lys Ala Arg
1               5

(2) INFORMATION FOR SEQ ID NO: 250:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 250:

Glu Asp Glu Ala Gly Asp Glu Asp Glu Leu
1               5                   10

(2) INFORMATION FOR SEQ ID NO: 251:

(i) SEQUENCE CHARACTERISTICS:
        (A) LENGTH: 23
        (B) TYPE: amino acid
        (C) STRANDEDNESS: single
        (D) TOPOLOGY: linear (xi) SEQUENCE DESCRIPTION: SEQ ID NO: 251:

Arg Lys Arg Asn Lys Ala Arg Tyr Ser Pro Leu His
1               5                   10
Asn Glu Asp Glu Ala Gly Asp Glu Asp Glu Leu
            15                  20

(2) INFORMATION FOR SEQ ID NO: 252:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 252:

Lys Glu Glu Ala Glu Lys Lys Ala Ala Glu Gln Arg
1               5                   10

(2) INFORMATION FOR SEQ ID NO: 253:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 253:

His Ala Asp Arg Arg Leu Met Glu
1               5

(2) INFORMATION FOR SEQ ID NO: 254:

```
        (i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 254:

Asp Val Glu Arg Gln Ser Thr Asp Ala Lys
1               5                   10

(2) INFORMATION FOR SEQ ID NO: 255:

(i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 255:

Lys Ile Glu Gly Asp Leu Lys Lys
1               5

(2) INFORMATION FOR SEQ ID NO: 256:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 256:

Glu Leu Arg Pro Gln Leu Glu Glu Ala Asp
1               5                   10

(2) INFORMATION FOR SEQ ID NO: 257:

(i) SEQUENCE CHARACTERISTICS:
            (A) LENGTH: 12
            (B) TYPE: amino acid
            (C) STRANDEDNESS: single
            (D) TOPOLOGY: linear (xi) SEQUENCE DESCRIPTION: SEQ ID NO: 257:

Asp Ser Gln Tyr Gln Glu Ala Arg Glu Ala Glu Glu
1               5                   10

(2) INFORMATION FOR SEQ ID NO: 258:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 258:

Arg Leu Lys Lys Thr Glu Ala Glu Lys
1               5

(2) INFORMATION FOR SEQ ID NO: 259:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 259:
```

```
Ala Lys Thr Lys Gln Lys Ala
1               5
```

(2) INFORMATION FOR SEQ ID NO: 260:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 260:

```
Asp Leu Ala Arg Ser Ala Asp Lys Ser
1               5
```

(2) INFORMATION FOR SEQ ID NO: 261:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 261:

```
Lys Glu Pro Ile Glu Val Glu Pro Leu Pro Asn Asp
1               5                   10
Arg
```

(2) INFORMATION FOR SEQ ID NO: 262:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 262:

```
Arg Val Gln Ser Arg Gly Val Glu Asp Gly Gly Arg
1               5                   10
Ser Pro Lys
        15
```

(2) INFORMATION FOR SEQ ID NO: 263:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 263:

```
Glu Ser His Gln Val Glu Lys Arg Lys
1               5
```

(2) INFORMATION FOR SEQ ID NO: 264:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 264:

```
Asn Pro Gln Met Asp Lys Arg Lys
1               5
```

(2) INFORMATION FOR SEQ ID NO: 265:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 265:

Asp His Arg Val Asp Lys Arg Lys
1               5

(2) INFORMATION FOR SEQ ID NO: 266:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 266:

Lys Arg Asn Ala Val Glu Val Leu Lys Arg Glu
1               5                   10

(2) INFORMATION FOR SEQ ID NO: 267:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 267:

Lys Arg Asn Val Ala Glu Asp Pro Asn Arg Glu
1               5                   10

(2) INFORMATION FOR SEQ ID NO: 268:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 268:

Arg Arg Asn Ala Glu Val Val Asp Val Glu
1               5                   10

(2) INFORMATION FOR SEQ ID NO: 269:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 269:

Leu Lys Asn Asp Gly Arg Gln Val Glu Lys Arg Arg
1               5                   10
Asn (2) INFORMATION FOR SEQ ID NO: 270:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 270:

Lys Asn Asp Gly Arg Gln Val Glu Lys Arg Arg
1               5                   10

(2) INFORMATION FOR SEQ ID NO: 271:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 271:

Lys Asp Asp Trp Arg Lys Ile Pro Lys Gln Arg
1               5                   10

(2) INFORMATION FOR SEQ ID NO: 272:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 272:

Lys Lys Val Glu Arg Gln Arg
1               5

(2) INFORMATION FOR SEQ ID NO: 273:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 273:

Asp Gly Val Pro Val Glu Lys Lys Arg
1               5

(2) INFORMATION FOR SEQ ID NO: 274:

(i) SEQUENCE CHARACTERISTICS:
        (A) LENGTH: 7
        (B) TYPE: amino acid
        (C) STRANDEDNESS: single
        (D) TOPOLOGY: linear (xi) SEQUENCE DESCRIPTION: SEQ ID NO: 274:

Arg Gly Asp His Arg Asp Asn
1               5

(2) INFORMATION FOR SEQ ID NO: 275:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 275:

Asp Glu His Glu Arg Trp
1               5

(2) INFORMATION FOR SEQ ID NO: 276:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 276:

Asp Glu Asp Asp Arg Trp Thr Lys Asp
1               5

(2) INFORMATION FOR SEQ ID NO: 277:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 277:

Glu Phe Ala Asp Arg Asp Glu Val Arg
1               5

(2) INFORMATION FOR SEQ ID NO: 278:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 278:

Glu Val Ala His Arg Asp Glu
1               5

(2) INFORMATION FOR SEQ ID NO: 279:

(i) SEQUENCE CHARACTERISTICS:
            (A) LENGTH: 9
            (B) TYPE: amino acid
            (C) STRANDEDNESS: single
            (D) TOPOLOGY: linear (xi) SEQUENCE DESCRIPTION: SEQ ID NO: 279:

Glu Val Ala Asp Arg Asp Glu Val Arg
1               5

(2) INFORMATION FOR SEQ ID NO: 280:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 280:

Arg Tyr Asp Glu Tyr Lys Arg
1               5

(2) INFORMATION FOR SEQ ID NO: 281:

(i) SEQUENCE CHARACTERISTICS:
            (A) LENGTH: 5
            (B) TYPE: amino acid
            (C) STRANDEDNESS: single
            (D) TOPOLOGY: linear (xi) SEQUENCE DESCRIPTION: SEQ ID NO: 281:

Arg Ser Gly Glu Pro (2) INFORMATION FOR SEQ ID NO: 282:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 282:

```
Arg Asn Gly Asp Gln Gln Gly Ile His His
1               5                   10
```

(2) INFORMATION FOR SEQ ID NO: 283:

(i) SEQUENCE CHARACTERISTICS:
        (A) LENGTH: 6
        (B) TYPE: amino acid
        (C) STRANDEDNESS: single
        (D) TOPOLOGY: linear (xi) SEQUENCE DESCRIPTION: SEQ ID NO: 283:

```
Ala Arg Gln Arg Arg Pro
1               5
```

(2) INFORMATION FOR SEQ ID NO: 284:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 284:

```
Arg Asp Asp Asn Asp Arg Asp Pro Ser Ala Lys
1               5                   10
```

(2) INFORMATION FOR SEQ ID NO: 285:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 285:

```
Lys Val Ser Lys Arg Pro Asp Tyr Asp
1               5
```

(2) INFORMATION FOR SEQ ID NO: 286:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 286:

```
Glu Ala Phe Glu Cys Phe Glu Ser Asp Pro Asn Ala
1               5                   10
Lys
```

(2) INFORMATION FOR SEQ ID NO: 287:

(i) SEQUENCE CHARACTERISTICS:
        (A) LENGTH: 10

(B) TYPE: amino acid
        (C) STRANDEDNESS: single
        (D) TOPOLOGY: linear (xi) SEQUENCE DESCRIPTION: SEQ ID NO: 287:

Lys Cys Arg Lys Lys Tyr Glu Phe Cys Arg
1               5                   10

(2) INFORMATION FOR SEQ ID NO: 288:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 288:

His Arg His Gln Arg Thr Pro Glu Asn Tyr Pro Asn
1               5                   10
Asp (2) INFORMATION FOR SEQ ID NO: 289:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 289:

Asp Pro Ser Ile Arg Trp Glu Tyr Cys
1               5

(2) INFORMATION FOR SEQ ID NO: 290:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 290:

His Gln His Lys Arg Thr Pro Glu Asn His Pro Asn
1               5                   10
Asp Asp (2) INFORMATION FOR SEQ ID NO: 291:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 291:

Met Asp Pro Ser Val Arg Arg Glu Tyr Cys
1               5                   10

(2) INFORMATION FOR SEQ ID NO: 292:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 292:

```
Arg Thr Pro Glu Asn Tyr Pro Asn Gly
1               5
```

(2) INFORMATION FOR SEQ ID NO: 293:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 293:

```
Leu Glu Ala Pro Ser Lys Gln Ala
1               5
```

(2) INFORMATION FOR SEQ ID NO: 294:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 294:

```
Leu Glu Ala Phe Leu Gln Glu Pro Thr Glu Glu
1               5                   10
```

(2) INFORMATION FOR SEQ ID NO: 295:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 295:

```
Gly His Leu Ala Gly Gly Thr Asp Arg
1               5
```

(2) INFORMATION FOR SEQ ID NO: 296:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 296:

```
Glu Arg Arg Lys Asp Arg Gly Gly Arg Glu Asp
1               5                   10
```

(2) INFORMATION FOR SEQ ID NO: 297:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 297:

```
Glu Ser Arg Lys Asn Arg Gly Gly Arg Glu Glu
1               5                   10
```

(2) INFORMATION FOR SEQ ID NO: 298:

(i) SEQUENCE CHARACTERISTICS:
        (A) LENGTH: 11

```
        (B) TYPE: amino acid
        (C) STRANDEDNESS: single
        (D) TOPOLOGY: linear (xi) SEQUENCE DESCRIPTION: SEQ ID NO: 298:

Glu Ser Lys Gly Lys Arg Ala Gly Arg Glu Gln
1               5                   10

(2) INFORMATION FOR SEQ ID NO: 299:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 299:

Lys Glu Gly Phe Arg Asn Lys Val Pro Cys Leu Gln
1               5                   10
Glu (2) INFORMATION FOR SEQ ID NO: 300:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 300:

Gly Glu Glu Glu Leu Arg Arg Arg Leu Arg
1               5                   10

(2) INFORMATION FOR SEQ ID NO: 301:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 301:

His Glu Arg Glu Glu Glu Leu Arg Lys Arg Leu Arg
1               5                   10

(2) INFORMATION FOR SEQ ID NO: 302:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 302:

Thr Glu Glu Glu Leu Arg Arg Arg Leu Arg
1               5                   10

(2) INFORMATION FOR SEQ ID NO: 303:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 303:

Asn Glu Glu Glu Leu Arg Arg Arg Leu Arg
```

(2) INFORMATION FOR SEQ ID NO: 304:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 304:

Glu Arg Ala Asp Glu Glu Gly Leu Gln Gly Lys Leu
1               5                   10
Arg (2) INFORMATION FOR SEQ ID NO: 305:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO: 305:

Asp Ser Asp Glu Glu Leu Leu Arg Thr Val Arg
1               5                   10

(2) INFORMATION FOR SEQ ID NO: 306:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 306:

Glu Pro Gln Asp Asp Ala Arg Leu Leu Gln Ala Val
1               5                   10
Lys (2) INFORMATION FOR SEQ ID NO: 307:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 307:

Pro Glu Glu Arg Arg Leu Leu Asx
1               5

(2) INFORMATION FOR SEQ ID NO: 308:

(i) SEQUENCE CHARACTERISTICS:
        (A) LENGTH: 10
        (B) TYPE: amino acid
        (C) STRANDEDNESS: single
        (D) TOPOLOGY: linear (xi) SEQUENCE DESCRIPTION: SEQ ID NO: 308:

Trp Arg Asp Met Glu Pro Pro Leu Arg Glu
1               5                   10

(2) INFORMATION FOR SEQ ID NO: 309:

```
        (i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 309:

Trp Arg Asp Met Glu Pro Pro Leu Arg Glu
1               5                   10

(2) INFORMATION FOR SEQ ID NO: 310:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 310:

Gln Lys Ser Met Glu Pro Pro Leu Arg Glu
1               5                   10

(2) INFORMATION FOR SEQ ID NO: 311:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 311:

Lys Lys Lys Arg Gly Trp Tyr Lys Trp Leu Arg Lys
1               5                   10
Leu (2) INFORMATION FOR SEQ ID NO: 312:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 312:

Lys Arg Arg Lys Gly Trp Phe Gln Trp Leu Arg Lys
1               5                   10
Leu (2) INFORMATION FOR SEQ ID NO: 313:

(i) SEQUENCE CHARACTERISTICS:
            (A) LENGTH: 15
            (B) TYPE: amino acid
            (C) STRANDEDNESS: single
            (D) TOPOLOGY: linear (xi) SEQUENCE DESCRIPTION: SEQ ID NO: 313:

Asp Arg Val Tyr Ile His Pro Phe His Leu Leu Tyr
1               5                   10
His Asn Lys
        15

(2) INFORMATION FOR SEQ ID NO: 314:

(i) SEQUENCE CHARACTERISTICS:
            (A) LENGTH: 15
```

```
            (B) TYPE: amino acid
            (C) STRANDEDNESS: single
            (D) TOPOLOGY: linear (xi) SEQUENCE DESCRIPTION: SEQ ID NO: 314:

Asp Arg Val Tyr Ile His Pro Phe His Leu Leu Tyr
1               5                   10

Tyr Ser Lys
        15

(2) INFORMATION FOR SEQ ID NO: 315:

(i) SEQUENCE CHARACTERISTICS:
            (A) LENGTH: 15
            (B) TYPE: amino acid
            (C) STRANDEDNESS: single
            (D) TOPOLOGY: linear (xi) SEQUENCE DESCRIPTION: SEQ ID NO: 315:

Asp Arg Val Tyr Ile His Pro Phe His Leu Val Ile
1               5                   10

His Asn Glu
        15

(2) INFORMATION FOR SEQ ID NO: 316:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 316:

Glu Asn Pro Ser Val Glu Thr Leu Pro Glu Ser Thr
1               5                   10
Phe (2) INFORMATION FOR SEQ ID NO: 317:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 317:

Glu Asn Pro Ser Val Glu Thr Leu Pro Glu Pro Thr
1               5                   10
Phe (2) INFORMATION FOR SEQ ID NO: 318:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 318:

Ala Lys Ala Asn Ala Gly Lys Pro Lys Asp Pro Thr
1               5                   10
Phe (2) INFORMATION FOR SEQ ID NO: 319:
```

(i) SEQUENCE CHARACTERISTICS:
            (A) LENGTH: 11
            (B) TYPE: amino acid
            (C) STRANDEDNESS: single
            (D) TOPOLOGY: linear (xi) SEQUENCE DESCRIPTION: SEQ ID NO: 319:

Lys Leu Ser Asn Asp Arg Ile Arg Val Gly Glu
1               5                   10

(2) INFORMATION FOR SEQ ID NO: 320:

(i) SEQUENCE CHARACTERISTICS:
            (A) LENGTH: 11
            (B) TYPE: amino acid
            (C) STRANDEDNESS: single
            (D) TOPOLOGY: linear (xi) SEQUENCE DESCRIPTION: SEQ ID NO: 320:

Lys Met Gly Asp Thr Asn Pro Arg Val Gly Glu
1               5                   10

(2) INFORMATION FOR SEQ ID NO: 321:

(i) SEQUENCE CHARACTERISTICS:
            (A) LENGTH: 11
            (B) TYPE: amino acid
            (C) STRANDEDNESS: single
            (D) TOPOLOGY: linear (xi) SEQUENCE DESCRIPTION: SEQ ID NO: 321:

Asn Ile Gly Asp Thr Asn Pro Arg Val Gly Glu
1               5                   10

(2) INFORMATION FOR SEQ ID NO: 322:

(i) SEQUENCE CHARACTERISTICS:
            (A) LENGTH: 11
            (B) TYPE: amino acid
            (C) STRANDEDNESS: single
            (D) TOPOLOGY: linear (xi) SEQUENCE DESCRIPTION: SEQ ID NO: 322:

Glu Leu Glu Ala Asp Glu Arg Glu Pro Thr Glu
1               5                   10

(2) INFORMATION FOR SEQ ID NO: 323:

(i) SEQUENCE CHARACTERISTICS:
            (A) LENGTH: 7
            (B) TYPE: amino acid
            (C) STRANDEDNESS: single
            (D) TOPOLOGY: linear (xi) SEQUENCE DESCRIPTION: SEQ ID NO: 323:

Asp Gly Trp Arg Arg Met Pro
1               5

(2) INFORMATION FOR SEQ ID NO: 324:

(i) SEQUENCE CHARACTERISTICS:
            (A) LENGTH: 6
            (B) TYPE: amino acid
            (C) STRANDEDNESS: single
            (D) TOPOLOGY: linear (xi) SEQUENCE DESCRIPTION: SEQ ID NO: 324:

```
Asp Arg Arg Arg Met Pro
1               5
```

(2) INFORMATION FOR SEQ ID NO: 325:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 325:

```
Lys Arg Ile Phe Leu Lys Arg Met Pro Ser Ile Arg
1               5                   10
Glu
```

(2) INFORMATION FOR SEQ ID NO: 326:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO: 326:

```
Gly Arg Ile Leu Leu Lys Lys Met Pro Ser Val Arg
1               5                   10
Glu
```

(2) INFORMATION FOR SEQ ID NO: 327:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 327:

```
Lys Arg Met Pro Ser Ile Arg Glu Ser Leu Lys Glu
1               5                   10
Arg Gly
```

(2) INFORMATION FOR SEQ ID NO: 328:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 328:

```
Lys Lys Met Pro Ser Val Arg Glu Ile Leu Glu Glu
1               5                   10
Arg Gly
```

(2) INFORMATION FOR SEQ ID NO: 329:

(i) SEQUENCE CHARACTERISTICS:
        (A) LENGTH: 8
        (B) TYPE: amino acid
        (C) STRANDEDNESS: single
        (D) TOPOLOGY: linear (xi) SEQUENCE DESCRIPTION: SEQ ID NO: 329:

```
Arg Glu Ile Leu Glu Glu Arg Gly
```

(2) INFORMATION FOR SEQ ID NO: 330:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 330:

Arg Leu Gly Pro Glu Trp Ser Gln Pro Met Lys Arg
1               5                   10

(2) INFORMATION FOR SEQ ID NO: 331:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 331:

Arg Ile Ser Ala Glu Trp Gly Glu Phe Ile Lys Lys
1               5                   10

(2) INFORMATION FOR SEQ ID NO: 332:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 332:

Arg Ile Ser Ala Glu Trp Gly Glu Phe Ile Lys Lys
1               5                   10

(2) INFORMATION FOR SEQ ID NO: 333:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 333:

Arg Leu Ser Ala Glu Trp Gly Val Phe Thr Lys Arg
1               5                   10

(2) INFORMATION FOR SEQ ID NO: 334:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO: 334:

His Lys Leu Phe Asp Ala Ser Asp Ser Ser Ser Tyr
1               5                   10
Lys His (2) INFORMATION FOR SEQ ID NO: 335:

(i) SEQUENCE CHARACTERISTICS:
        (A) LENGTH: 14

```
            (B) TYPE: amino acid
            (C) STRANDEDNESS: single
            (D) TOPOLOGY: linear (xi) SEQUENCE DESCRIPTION: SEQ ID NO: 335:

His  Asn  Leu  Tyr  Asp  Ser  Ser  Glu  Ser  Ser  Ser  Tyr
1                  5                        10

Met  Glu (2) INFORMATION FOR SEQ ID NO: 336:

(i) SEQUENCE CHARACTERISTICS:
            (A) LENGTH: 14
            (B) TYPE: amino acid
            (C) STRANDEDNESS: single
            (D) TOPOLOGY: linear (xi) SEQUENCE DESCRIPTION: SEQ ID NO: 336:

His  Ser  Leu  Tyr  Glu  Ser  Ser  Asp  Ser  Ser  Ser  Tyr
1                  5                        10

Met  Glu (2) INFORMATION FOR SEQ ID NO: 337:

(i) SEQUENCE CHARACTERISTICS:
            (A) LENGTH: 17
            (B) TYPE: amino acid
            (C) STRANDEDNESS: single
            (D) TOPOLOGY: linear (xi) SEQUENCE DESCRIPTION: SEQ ID NO: 337:

Lys  Glu  Asp  Val  Phe  Ser  Phe  Ser  Phe  Tyr  Tyr  Asn
1                  5                        10

Arg  Asp  Ser  Glu  Asn
                15

(2) INFORMATION FOR SEQ ID NO: 338:

(i) SEQUENCE CHARACTERISTICS:
            (A) LENGTH: 14
            (B) TYPE: amino acid
            (C) STRANDEDNESS: single
            (D) TOPOLOGY: linear (xi) SEQUENCE DESCRIPTION: SEQ ID NO: 338:

Lys  Glu  Glu  Val  Phe  Ser  Val  Tyr  Tyr  Asn  Arg  Gly
1                  5                        10

Ser  His (2) INFORMATION FOR SEQ ID NO: 339:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 339:

Asp  Pro  Gln  His  Tyr  Glu  Gly  Asn  Phe  His
1                  5                        10

(2) INFORMATION FOR SEQ ID NO: 340:

(i) SEQUENCE CHARACTERISTICS:
            (A) LENGTH: 15
```

(B) TYPE: amino acid
        (C) STRANDEDNESS: single
        (D) TOPOLOGY: linear (xi) SEQUENCE DESCRIPTION: SEQ ID NO: 340:

Glu Lys Leu Met Glu Ala Leu Gly Ala Lys Lys Arg
1               5                   10

Leu Phe Asp
        15

(2) INFORMATION FOR SEQ ID NO: 341:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 341:

Gln Leu Ile Met Gln Ala Leu Gly Val Lys Glu Lys
1               5                   10

Arg Ala Asn
        15

(2) INFORMATION FOR SEQ ID NO: 342:

(i) SEQUENCE CHARACTERISTICS:
        (A) LENGTH: 15
        (B) TYPE: amino acid
        (C) STRANDEDNESS: single
        (D) TOPOLOGY: linear (xi) SEQUENCE DESCRIPTION: SEQ ID NO: 342:

Lys Leu Ile Met Gln Ala Leu Gly Ala Lys Glu Lys
1               5                   10

Arg Ile Glu
        15

(2) INFORMATION FOR SEQ ID NO: 343:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 343:

Asp Tyr Val Phe Gln Glu Ser Tyr Ser Ser Lys Lys
1               5                   10

(2) INFORMATION FOR SEQ ID NO: 344:

(i) SEQUENCE CHARACTERISTICS:
        (A) LENGTH: 12
        (B) TYPE: amino acid
        (C) STRANDEDNESS: single
        (D) TOPOLOGY: linear (xi) SEQUENCE DESCRIPTION: SEQ ID NO: 344:

Asp Tyr Val Gln Lys Asn Pro Phe Arg Asn Asp Asp
1               5                   10

(2) INFORMATION FOR SEQ ID NO: 345:

(i) SEQUENCE CHARACTERISTICS:
        (A) LENGTH: 11

```
            (B) TYPE: amino acid
            (C) STRANDEDNESS: single
            (D) TOPOLOGY: linear (xi) SEQUENCE DESCRIPTION: SEQ ID NO: 345:

Asp Tyr Val Gln Tyr Pro Asn Arg Arg Asp Lys
1               5                   10

(2) INFORMATION FOR SEQ ID NO: 346:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 346:

Arg Lys Phe Tyr Thr Glu Phe Asp Arg Arg Asn Asn
1               5                   10
Arg (2) INFORMATION FOR SEQ ID NO: 347:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 347:

Arg Lys Phe Tyr Thr Glu Phe Asp Arg His Asn Asn
1               5                   10
Arg (2) INFORMATION FOR SEQ ID NO: 348:

(i) SEQUENCE CHARACTERISTICS:
            (A) LENGTH: 13
            (B) TYPE: amino acid
            (C) STRANDEDNESS: single
            (D) TOPOLOGY: linear (xi) SEQUENCE DESCRIPTION: SEQ ID NO: 348:

Arg Lys Phe Tyr Thr Glu Phe Asp Arg His Asn Asn
1               5                   10
Arg (2) INFORMATION FOR SEQ ID NO: 349:

(i) SEQUENCE CHARACTERISTICS:
            (A) LENGTH: 12
            (B) TYPE: amino acid
            (C) STRANDEDNESS: single
            (D) TOPOLOGY: linear (xi) SEQUENCE DESCRIPTION: SEQ ID NO: 349:

Arg Tyr Leu Glu Leu Arg Glu Ala Ala Asp Tyr Asp
1               5                   10

(2) INFORMATION FOR SEQ ID NO: 350:

(i) SEQUENCE CHARACTERISTICS:
            (A) LENGTH: 12
            (B) TYPE: amino acid
            (C) STRANDEDNESS: single
            (D) TOPOLOGY: linear
```

(xi) SEQUENCE DESCRIPTION: SEQ ID NO: 350:

Arg Tyr Leu Glu Val Gln Glu Ala Ala Val Tyr Asp
1               5                   10

(2) INFORMATION FOR SEQ ID NO: 351:

(i) SEQUENCE CHARACTERISTICS:
      (A) LENGTH: 12
      (B) TYPE: amino acid
      (C) STRANDEDNESS: single
      (D) TOPOLOGY: linear (xi) SEQUENCE DESCRIPTION: SEQ ID NO: 351:

Lys Arg Asp Val Ala Gly Glu Gln Pro Tyr Arg Arg
1               5                   10

(2) INFORMATION FOR SEQ ID NO: 352:

(i) SEQUENCE CHARACTERISTICS:
      (A) LENGTH: 12
      (B) TYPE: amino acid
      (C) STRANDEDNESS: single
      (D) TOPOLOGY: linear (xi) SEQUENCE DESCRIPTION: SEQ ID NO: 352:

Lys Arg Asn Leu Ala Glu Glu Gln Pro Tyr Arg Arg
1               5                   10

(2) INFORMATION FOR SEQ ID NO: 353:

(i) SEQUENCE CHARACTERISTICS:
      (A) LENGTH: 9
      (B) TYPE: amino acid
      (C) STRANDEDNESS: single
      (D) TOPOLOGY: linear (xi) SEQUENCE DESCRIPTION: SEQ ID NO: 353:

Asp His Pro Leu Pro Ser Ala Glu Arg
1               5

(2) INFORMATION FOR SEQ ID NO: 354:

(i) SEQUENCE CHARACTERISTICS:
      (A) LENGTH: 9
      (B) TYPE: amino acid
      (C) STRANDEDNESS: single
      (D) TOPOLOGY: linear (xi) SEQUENCE DESCRIPTION: SEQ ID NO: 354:

Asp His Pro Leu Pro Thr Arg Glu Arg
1               5

(2) INFORMATION FOR SEQ ID NO: 355:

(i) SEQUENCE CHARACTERISTICS:
      (A) LENGTH: 8
      (B) TYPE: amino acid
      (C) STRANDEDNESS: single
      (D) TOPOLOGY: linear (xi) SEQUENCE DESCRIPTION: SEQ ID NO: 355:

Arg Arg Ser Ile Arg Ser Ser Gln
1               5

(2) INFORMATION FOR SEQ ID NO: 356:

```
        (i) SEQUENCE CHARACTERISTICS:
            (A) LENGTH: 8
            (B) TYPE: amino acid
            (C) STRANDEDNESS: single
            (D) TOPOLOGY: linear (xi) SEQUENCE DESCRIPTION: SEQ ID NO: 356:

Arg Arg Ser Val Thr Ser Ser Gln
1               5

(2) INFORMATION FOR SEQ ID NO: 357:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 357:

Asp Pro Ser Lys Met Thr Pro Leu Ala Asp
1               5                   10

(2) INFORMATION FOR SEQ ID NO: 358:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 358:

Asp Thr Ser Lys Met Met Leu Leu Val Asp
1               5                   10

(2) INFORMATION FOR SEQ ID NO: 359:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 359:

Glu Pro Tyr Glu Leu Glu Asn Pro Asn Gly
1               5                   10

(2) INFORMATION FOR SEQ ID NO: 360:

(i) SEQUENCE CHARACTERISTICS:
            (A) LENGTH: 10
            (B) TYPE: amino acid
            (C) STRANDEDNESS: single
            (D) TOPOLOGY: linear (xi) SEQUENCE DESCRIPTION: SEQ ID NO: 360:

Glu Pro Leu Glu Leu Glu Thr Ser Thr Arg
1               5                   10
```

METHOD OF PRODUCING VACCINES FROM PROTEIN SIGNAL OLIGOPEPTIDES

CROSS-REFERENCE TO RELATED APPLICATIONS

The present application is a continuation-in-part of U.S. application Ser. No. 09/881,976, filed Jun. 15, 2001, now abandoned, which is a continuation of U.S. application Ser. No. 09/232,186, filed on Jan. 14, 1999, now abandoned, which is a continuation-in-part of U.S. patent application Ser. No. 08/704,499, filed on Aug. 28, 1996, now abandoned, which is a U.S.C. 371 of PCT/US95/00575, filed Jan. 12, 1995, which is a continuation of U.S. patent application Ser. No. 08/182,248, filed Jan. 14, 1994, now abandoned, all of which are incorporated herein by reference.

BACKGROUND

The discovery of the genetic code by Watson and Crick four decades ago defined the principles by which genes (the genetic code) encode for proteins by determining the sequence of amino acids. As is known, proteins are important carriers of metabolic information in living organisms. Exogenous protein organisms such as the HIV virus, and other endogenous proteins such as that which causes diabetes, are also the cause of many human diseases.

The genetic code determines the structure of proteins, thereby dictating the function of the protein. In the vast majority of proteins, biological activity and the specific function of the protein is primarily mediated via specific amino acid sequences located on the outside surface of the three dimensional protein.

The protein code determines the relation between structure and function within a protein sequence and, thereby effects a specific biological action. Therefore, the protein code is the biological language for protein-mediated information transfer during health and disease. The interaction of hormones and other ligands with their respective receptors, of enzymes with protein substrates, of adhesive proteins with integrins, and of antibodies with antigens, as well as other protein actions and interactions are determined by the same structure/function principles and the same biological language. The protein code also provides a missing link in the regulation of protein synthesis. Proteins also have important feed-back functions directly or indirectly modulating the synthesis rate of that protein. The structure/function relation of proteins, which determines protein actions and interactions, are hereafter referred to as the protein code.

Conventional drug therapy is frequently compromised by an unknown therapeutic mechanism and by a wide range of side effects and considerable toxicity. Conventional gene therapy uses some of the protein interaction principles mentioned above to increase the therapeutic specificity of the pharmaceutical and the delivery of the drug to the target cells and organs, which results in a reduction in toxicity and safety compared to conventional drug therapy. However, gene therapy has its disadvantages as it requires that the specific sequence of the entire disease causing protein be determined. That is, in order to treat or fight a disease, scientists attempt to determine the genetic code by replicating the entire amino acid sequence of the disease causing protein. Gene therapy is compromised by its technological requirements and its high cost. The development of gene therapy drugs is a time consuming process through the research and development phase of the drug, the clinical studies phase, as well as in the drug manufacturing and therapy phase of the drugs so developed. For example, in gene therapy, identification of the target disease causing proteins spans anywhere from months to years. The production of a drug, in-vitro tests, in-vivo tests alone takes approximately another several years. First clinical studies span between 5 to 10 years. This causes drugs developed through gene therapy to be very expensive, and restricts its therapeutic application to only certain more profitable and exclusive areas of diseases in the foreseeable future.

Therefore, there is a need for a method of therapy that allows for the interception of pathological interactions with maximum effectiveness.

There is a further need for a method of therapy that enables maximum therapeutic specificity, based on the precise structure/function relation of specific oligopeptide signals.

Yet another need is for a method of therapy that is safe and eliminates or limits toxicity, and allows for controlling undesired biological side-effects by optimizing the length and composition of the therapeutic peptide.

There is also a need for a therapy method that reduced the time and expense of development of therapeutic peptides to a fraction of conventional gene therapeutic research and development. Most importantly, there is a need for a targeted and safe therapy method which will allow clinical application of drugs for a variety of disease causing proteins that have been ignored because of the cost of development.

SUMMARY

Just as the human language allows for communication and interaction among humans, the protein code is the underlying communication means for the interaction of antigens with antibodies, enzymes with substrates, receptors with ligands, adhesion molecules with integrins and other forms of protein communication. Humans communicate through sentences. Sentences are in turn composed of words and words are in turn made of letters. Similarly, the three dimentional structure of proteins can be analogized to sentences through which protein communication takes place. The peptide sequence of the protein can be analogized to words in the sentence, and the individual amino acids of the protein can be analogized to letters in words. However, what today remains a mystery in the language of communication in proteins are the "verbs" of the protein code sentences.

The description discloses a method of producing therapeutic peptides as vaccines in the prevention of human disease which are caused by one or more proteins. This method of peptide therapy, in contrast to gene therapy, comprises identifying the protein responsible for causing the human disease; identifying one or more signal oligopeptide sequences within the structure of the disease causing protein, the one or more signal oligopeptides representing the amino acid sequence of maximum hydrophilicity; and synthesizing one or more vaccine oligopeptides, the vaccine oligopeptides having amino acid sequences corresponding to the amino acid sequences of the signal oligopeptides of maximum hydrophilicity.

In an alternative embodiment the method further comprises a method of identifying one or more signal oligopeptide sequences within the structure of the disease causing protein, the one or more signal oligopeptides representing the amino acid sequence of maximum surface probability of the amino acids in the disease causing protein. The area of maximum surface probability defined as that portion of the amino acid sequence that has a higher probability of being on the surface of the protein.

In an alternative embodiment, the method further comprises a method of identifying one or more signal oligopeptide sequences within the structure of the disease causing protein, the one or more signal oligopeptides representing the amino acid sequence of maximum electrical charge of the amino acids in the disease causing protein.

The method further comprising an optimization step, wherein the one or more vaccine oligopeptides are manipulated through one or more amino acid residue substitutions, amino acid deletions, or amino acid insertions, or any combination thereof, to produce an optimized immunogenic response in vaccinated humans.

Preferably, the method of the invention comprises a method wherein immunogenic response of the vaccine oligopeptides in humans is enhanced by repetition of the vaccine oligopeptides to form a linear polypeptide.

Also, preferably, the method of the invention comprises a method wherein the immunogenic response of the vaccine oligopeptides in humans is enhanced by repetition of the vaccine oligopeptides to form a cyclic polypeptide.

In yet another preferred embodiment, the method of the invention comprises a method wherein the immunogenic response of the vaccine oligopeptides in humans is enhanced by coupling of one or more of the vaccine oligopeptides to an immunogenic protein or non-protein haptens.

In yet another embodiment of the invention, the method of the invention comprises a method wherein the area of maximum hydrophilicity is identified by one or more hydrophilicity determining algorithms such as those identified in Table 1.

Advantages of Peptide Therapy over Gene Therapy and Drug Therapy

Peptide therapy will open a new field of therapeutic options in medicine. For the first time, it will be possible to develop specific therapeutic agents, which target only the affected organ or cell system, without any side effects. Of particular advantage is the fast identification of the therapeutic peptides, its short development phase and the resultant low cost. Furthermore, this new therapeutic technology will allow for the control of many diseases that are currently untreatable.

The benefits of peptide therapy become more obvious especially when compared to gene therapy. Gene therapy requires that first a gene specific for a given disease be identified. Once identified, then the process requires that it be artificially reproduced and then it be re-introduced into the patient's body. This procedure is both time consuming and its outcome is indeterminable. Thus, the therapeutic efficacy of gene therapy, can only be achieved after years of research and development and treatment, if at all.

In contrast, peptide therapy is based on the principle that at some point, the genetic code must be translated into proteins that then interact with cells, and that heath or disease is ultimately decided at the level of proteins. The identification and therapeutic use of the key oligopeptides within a selected protein is the most direct, specific, effective, as well as the safest and most affordable way for the prevention or treatment of the disease. Compared to gene therapy, the application of peptide therapy will shorten the time for development and treatment for many human diseases. Therefore, peptide therapy as described below has the following advantages.

Peptide therapy is a highly effective form of treatment. The discovery of the peptide code provides the rationale for deciphering the communication code of proteins in health and disease. This discovery is used therapeutically to intercept pathological interactions of human disease with maximum effectiveness.

Peptide therapy also enables maximum therapeutic specificity. Based on the precise understanding of the structure/function relation of specific protein signals, peptide therapy allows therapeutic targeting with unprecedented specificity.

Furthermore, peptide therapy is extremely safe. The use of synthetic analogs to physiologic compounds essentially-eliminates the problem of toxicity. Possible undesired biological side-effects are controllable by optimizing the length and composition of the therapeutic peptide.

Time and expenses for the development of therapeutic peptides is a fraction of conventional therapeutic research and development. Identification of potential therapeutic peptides takes minutes; in vitro screening of potential peptides is a matter of weeks; animal studies should provide first in vivo results within a few months. Most importantly, the unprecedented specificity and safety background of peptide therapy will allow clinical studies without delay.

The advantages of peptide therapy become even more obvious when this novel therapeutic approach is compared to conventional therapies. Conventional drug therapy is frequently compromised by an unknown therapeutic mechanism and by a wide range of side effects and considerable toxicity. Gene therapy is compromised by limited availability, its technological requirements and its high costs, which restricts its therapeutic application to exclusive areas in the foreseeable future. Heterologous or synthetic antibody therapy, the therapeutic application of antibodies produced outside of the patient's body, can cause incalculable adverse reactions by the patient's immune system against these 'foreign' antibodies. In contrast, peptide therapy makes elegant use of the patient's own immune system thereby excluding adverse immunological reactions.

BRIEF DESCRIPTION OF TABLES AND FIGURES

Table 1; shows the various amino acids found in proteins and their hydrophilicity and surface probability values.

FIGS. 1A and 1B show several of the protein code interaction principles including legibility, accessibility, variability, and specificity. FIG. 1C shows the oppositely charged amino acids can attract each other thereby enhancing confirmational specificity. FIG. 1D shows vaccines stimulating the production of antibodies which block pathological communication pathways not only in the prevention and treatment of infectious diseases but also in the therapy of neoplastic diseases, metabolic disorders and other diseases.

FIG. 2 shows the method of this invention used in peptide therapy in diabetes. This figure shows the three hydrophilicity peaks in the glucagon precursor sequence (A,B,C).

FIG. 3 shows Peptide therapy in HIV infections. Synthetic analogs to signal oligopeptides of the HIV envelope protein GP 160 or the cell receptor CD4 are used as vaccines. The hydrophylicity blot revealing potential signal oligopeptide sequences of GP 160 is shown in the upper part of FIG. 3. [I don't have this]

FIG. 8 shows the method of the present invention as described in Example No. 1

DETAILED DESCRIPTION

Figure 1A:
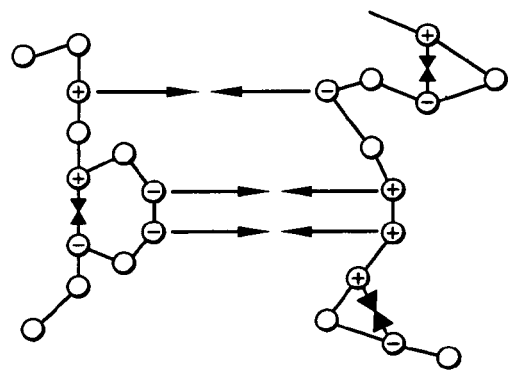

Infectious diseases, cancer, cardiovascular and other human diseases develop by means of one or more pathogenicity-mediating proteins, or disease causing proteins. Blocking the action of these proteins allows the specific therapeutic interception of a pathological communication, thereby blocking disease propagation.

In the human language eliminating or changing the verb of a sentence renders the whole sentence meaningless. Similarly, blocking the protein code verbs (signal oligopeptide sequences) can be therapeutically used to block the undesired action or interaction of an entire protein. If the verb in any sentence is altered, i.e. change eating to walking, the entire meaning of the sentence changes, or the sentence is rendered unintelligible. These verbs of the protein code, referred to as signal oligopeptides, determine the very specific function of a protein. Similarly, if a signal oligopeptide is altered (or blocked) in any given protein, either that protein's function changes, or the protein is rendered function-less. Interference with signal oligopeptides, these verbs of the protein code sentences, can lead to substantial modification or loss of the biological message of a protein. This modification or loss of the biological message of the protein can be used in peptide therapy to the advantage of a patient.

The specific action of these oligopeptides is determined by a characteristic combination of shape and electrical charge (both anionic and cationic) within the same signal sequence. Protein information transfer and protein interaction is dependent on the accessibility of the signal oli: gopeptide sequence. Therefore, in the majority of proteins, the sequence signals are localized on the surface of the protein. Signal oligopeptides are enriched with charged amino acids such as cationic amino acid residues arginine and lysine and/or the anionic amino acid residues glutamate and aspartate. Sometimes, these signal oligopeptides are in a versatile arrangement with neutral spacer amino acids. Therefore, signal oligopeptide sequences are generally represented by the regions of maximum hydrophilicity on the surface of the protein molecule.

A new type of signal is represented by oligopeptides which obtain their characteristic conformation or shape by a specific arrangement of oppositely charged amino acid residues within this oligopeptide sequence. These residues with opposite charge can attract each other thereby modulating a characteristic folding of this signal sequence. For example, in the signal sequence RGD the cationic residue arginine and the anionic residue aspartate attract each other leading to a characteristic folding of this tripeptide around the 'spacer' residue glycine.

The specific metabolic function of a protein is dependent on the specificity of its biological signal oligopeptide. The signal character of a specific signal oligopeptide is determined by a characteristic combination of electrical charge with structural conformation. Within a protein, RGD and analogous tripeptides can serve as strong primary anchors while the specific biological message is mediated by additional longer and more complex signal oligopeptides.

Synthetic analogs of signal oligopeptide sequences are used therapeutically in several ways. First, synthetic analogs of signal oligopeptide sequences can be used as competitive inhibitors of pathological communication. Second, synthetic analogs of signal oligopeptides can be used as vaccines. This second therapeutic approach makes use of the fact that signal oligopeptides on the surface of the protein are identical with the antigenicity determining lepitopes of this protein. Thus, antibodies are interceptors of metabolic communication. Binding the signal oligopeptide sequence of a protein to antibodies and other mediators of immune response reduces or blocks its metabolic interaction. If synthetic analogs to signal oligopeptides are used as vaccines it is necessary to render these peptides antigenic and to allow their discrimination as 'non-self. Synthetic analogs to signal oligopeptides can be rendered immunogenic by coupling them to haptens or by other conventional methods.

The method of this invention using synthetic analogs is based on the discovery of the primary structural principles determining immunogenicity. The discrimination between self and non-self between species of animals and humans is primarily based on amino acid residue substitutions or other residue variations within the signal oligopeptide sequences of a protein. By making use of this discovery effective therapeutic signal oligopeptides can be rapidly produced in the following way: signal oligopeptides of a given protein in one species of animals are the antigenicity determinants of this protein in another species of animals. To block the action of a pathogenicity-mediating or disease causing protein in the treatment of a human disease the synthetic signal oligopeptide vaccines are designed by copying corresponding amino acid signal sequences from another species. A glucagon signal oligopeptide vaccine for the treatment of diabetic patients would be based on glucagon signal sequences from rabbits, sheep, mice or other species. A titration of the therapeutic efficiency is possible using the evolutionary chain method described below. The greater the genetic and evolutionary distance of the selected animal species to humans the greater its antigenicity and, consequently, the greater its therapeutic efficiency as a vaccine.

Furthermore, signal oligopeptides of a protein are identical with the potential antigenic determinants. Antibodies and other mediators of immune response are interceptors of specific biological communication. Signal oligopeptides as promoters of differentiated protein communication and immune response mediators as interceptors form sophisticated network of biological communication. Therefore, decoding the physiologic aspects of this communication network will lead to a precise understanding of millions of metabolic interactions including the principles for development and differentiation of the body, which will lead to the therapeutic control of many diseases and eventually their eradication as causes of human mortality.

Figure 1B:
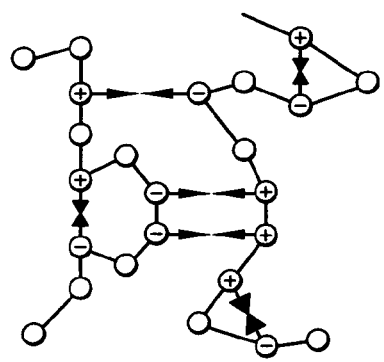
Figure 1C:
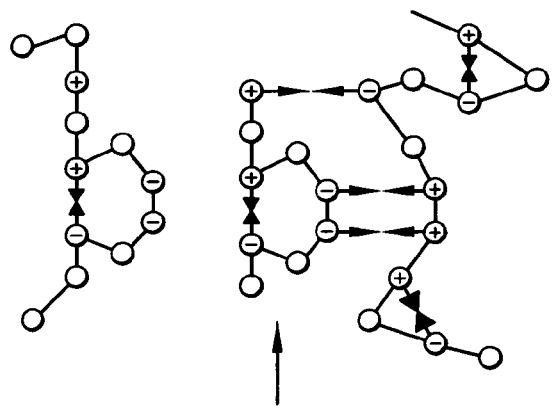
Figure 1D:
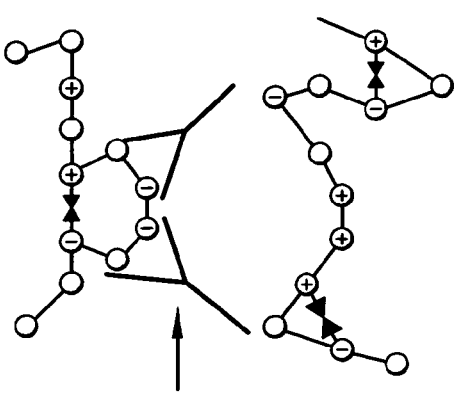

Turning now to the figures the invention is described in detail. FIGS. 1A and 1B show principles upon which the protein code functions. Within the amino acid sequence of a disease cause protein one or more signal oligopeptides represent the "verbs"—of the protein code which determine the specific action and interaction of that protein. This is referred to as the legibility of the protein. The signal oligopeptides of a protein are enriched in electrically charged amino acids (either cationic or anionic) and represent a segment of maximum hydrophylicity within the protein sequence. An infinite number of possible combinations between amino acids with different charges as well as neutral residues provide the variability for differentiated metabolic communication. The specificity of a signal sequence is the result of a characteristic combination of charge distribution and structural conformation within the signal oligopeptide sequence. FIG. 1B shows the oppositely charged amino acids attracting each other thereby enhancing conformational specificity. Signal oligopeptides mediate specific information transfer to their metabolic counterparts. Substitution, deletion or other amino acid residue variations within the signal sequence of a protein enable differentiation between 'self' and 'non-self'. Signal sequences are the antigenic epitopes of a protein and are responsible for potential immune responses when exposed to other organisms. Direct and indirect Peptide Interception Therapy (PIT) can be used to intercept undesired or pathological communication and thereby block the disease. FIG. 1C shows direct PIT synthetic analogs of signal oligopeptides used to competitively inhibit the interaction of proteins. Indirect PIT makes use of synthetic oligopeptides rendered immunogenic. FIG. 1D shows vaccines stimulating the production of antibodies which block pathological communication pathways not only in the prevention and treatment of infectious diseases but also in the therapy of neoplastic diseases, metabolic disorders and other diseases.

Peptide Interception Therapy (PIT)

The metabolic interaction of proteins is primarily modulated by one or more oligopeptide signal sequences which determine the metabolic interaction of a protein. Peptide Interception Therapy (PIT) is defined as the specific therapeutic interception of pathological or undesired protein actions and interactions by the therapeutic use of synthetic analogs to the signal oligopeptide sequences of this protein. To intercept the undesirable action of the disease causing protein, only the signal oligopeptide (protein verb) of the disease causing protein is therapeutically blocked.

First, using conventional methods, a disease causing protein, such as Glucogon, which mediates diabetes, is identified. These signal oligopeptide sequences are located on the surface of the disease causing protein and are represented by one or more sequences of maximum hydrophilicity region (e.g. hydrophilic maxima) or maximum electrical charge within the amino acid sequence of the protein. The signal oligopeptide sequences of this protein is identified from its primary structure by use of a protein data base in combination with a suitable algorithm, such as hydrophilicity or surface probability algorithms. Examples of hydrophilicity and surface probability algorithms are shown in Table 1. In this algorithm the highest hydrophilicity or probability values have to be assigned to the charged amino acids lysine, arginine, aspartate and glutamate followed by asparagine and glutamine.

Synthetic analogs to signal oligopeptide sequences can be therapeutically used to block the pathological effects of the disease causing protein. An unlimited number of signal oligopeptide analogs can be synthesized covering the entire sequence of a selected hydrophylicity peak or parts of it.

TABLE 1

The Maxims of the Following Algorithms -or Modifications Thereof-Can Be Used to Determine Potential Signal Oligopeptides In the Primary Structure of a Protein From a Protein Sequence Database

| Amino Acid Residue | A. Hydrophylicity Algorithm* | B. Surface Probability Algorithm** |
|---|---|---|
| Arginine | 3.0 | 9.5 |
| Aspartate | 3.0 | 8.1 |
| Glutamate | 3.0 | 8.4 |
| Lysine | 3.0 | 9.7 |
| Aspartate or Asparagine | 1.6 | 8.0 |
| Glutamate or Glutamine | 1.6 | 8.4 |
| Serine | 0.3 | 6.5 |
| Asparagine | 0.2 | 7.8 |
| Glutamine | 0.2 | 8.4 |
| Glycine | 0.0 | 4.8 |
| Proline | 0.0 | 7.5 |
| Threonine | -0.4 | 7.0 |
| Alanine | -0.5 | 4.9 |
| Histidine | -0.5 | 6.6 |
| Cysteine | -1.0 | 2.6 |
| Methionine | -1.3 | 4.8 |
| Valine | -1.5 | 3.6 |
| Isoleucine | -1.8 | 3.4 |
| Leucine | -1.8 | 4.0 |
| Tyrosine | -2.3 | 7.6 |
| Phenylalanine | -2.5 | 4.2 |
| Tryptophan | -3.4 | 5.1 |

C. Algorithm Based on the Following Amino Acid Categories:
1. Highest Values Assigned to Charged Amino Acids: Aspartate, Glutamate, Lysine, Arginine, Histidine
2. Medium Values Assigned to Uncharged Polar Amino Acids: Asparagine, Glutamine, Glycine, Cysteine, Serine, Threonine, Tyrosine
3. Lowest Values Assigned to Non Polar Amino Acids: Alanine, Valine, Leucine, Isoleucine, Proline, Phenylalanine, Methionine, Tryptophan
*According to HoppTP, Woods, KR. 1981. Proc. Natl. Acad. Sci. USA; 78: 3824-3828.
**Boger. Proceedings of the 1988 Miami Bio/Technology Winter Symposium. 10 Oxford and Washington. IRL Press.

Signal tetrapeptides, pentapeptides, hexapeptides and longer peptides represent primary candidates for specific peptide therapy. Shorter peptides, such as the tripeptide RGD, are less specific and ubiquitous side effects limit their broad therapeutic use.

Figure 2A:
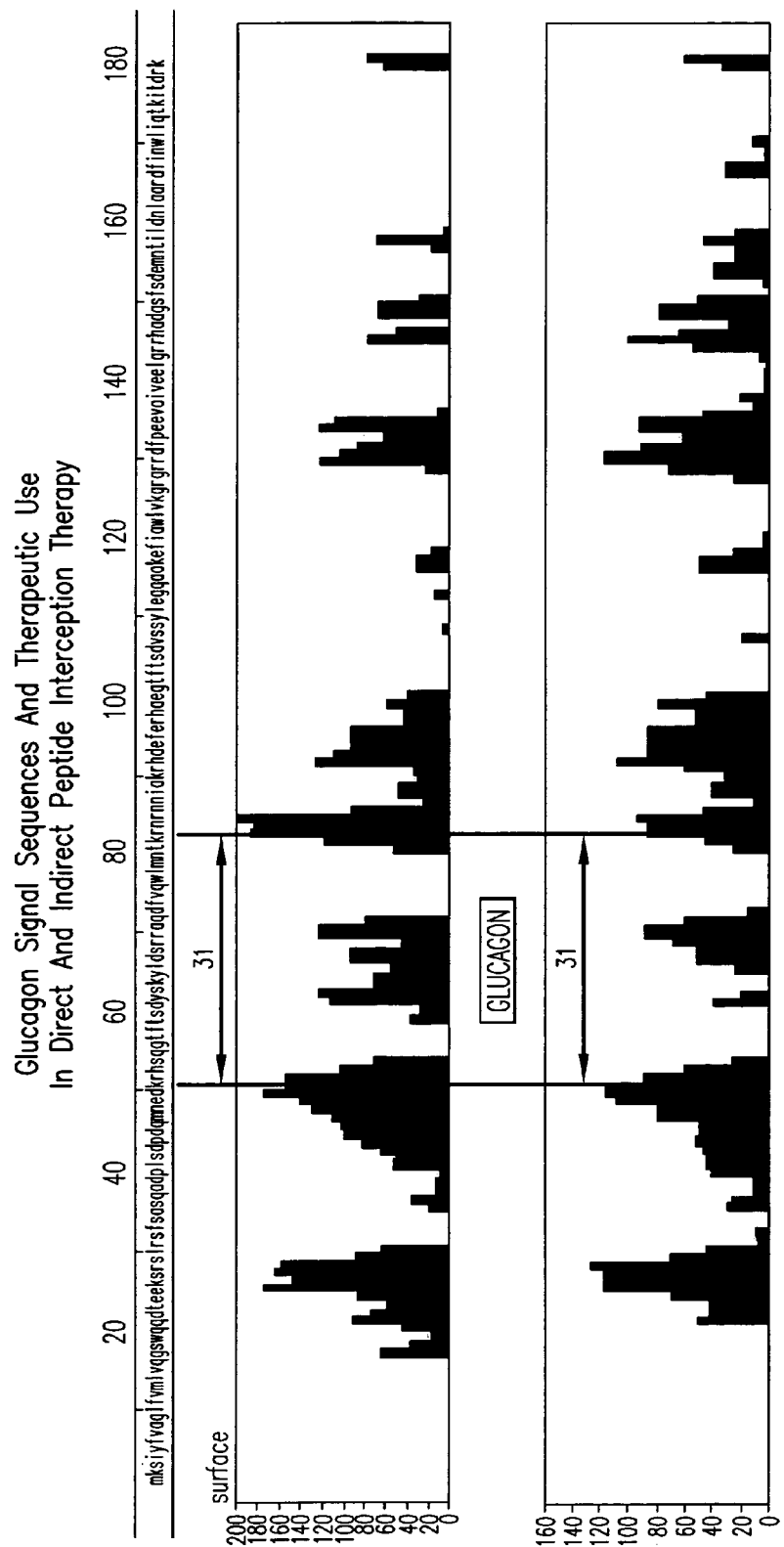

FIG. 2 shows the fundamentals of Peptide Interception Therapy (PIT). Proteins are essential carriers of specific metabolic information. Moreover, proteins are frequently mobile which makes them ideal and versatile communication molecules. This figure illustrates several key elements of direct PIT in peptide therapy. In conventional gene therapy, the entire three dimensional protein structure (protein sentence) is required to counter the effects of the disease causing protein. However, in direct peptide intercept therapy, only the signal oligopeptide sequence ("verb") has to be blocked. FIG. 2 also shows methods for identification, design, development and therapeutic use of synthetic analogs to signal oligopeptides in Peptide Interception Therapy as direct competitive inhibitors of selected protein actions.

As further described in detail below, peptide Interception Therapy (PIT) is used in two principal ways: direct PIT, which uses synthetic analogs of signal oligopeptides as competitive inhibitors of pathological or undesired metabolic interaction; and indirect PIT, which uses synthetic analogs as vaccines to stimulate the production of specific antibodies. In indirect PIT, antibodies developed from vaccines, not the therapeutic peptide itself, function as interceptors of protein communication.

Use of Signal Oligopeptide Sequences in Direct Peptide Interception Therapy (DPIT)

As indicated above, Direct Peptide Interception Therapy (Direct PIT) uses synthetic analogs of signal oligopeptides as direct competitive inhibitors for undesired protein communication. Direct blocking of pathogenicity mediating protein communication leads to the control of the related disease or clinical condition. This therapeutic approach is preferentially used in acute conditions, e.g. antithrombotic or fibrinolytic therapy. Direct PIT is preferentially used intravenously in higher therapeutic dosages of the synthetic peptide. Poly-oligopeptide analogs, time release delivery systems and other modifications of the peptide delivery mechanism are used to extend the range of various therapeutic applications.

FIG. 2 demonstrates a method of peptide therapy in diabetes and the signal sequences of proglucagon and therapeutic alternatives for peptide therapy in diabetic patients. Conventional treatment in diabetes focuses on increased availability of insulin. Peptide therapy enables an alternative approach. Synthetic analogs to the signal sequences of glucagon can be therapeutically used to attenuate the effect of this insulin antagonist. Note the three hydrophilicity peaks in the glucagon precursor sequence (A, B, C). The mature glucagon hormone is activated by contact and charge redistribution within peaks A and C. PIT therapy could have two distinct targets. First, blocking charge redistribution of precursor molecule (PIT for Peak A or C) prevents activation of the precursor to mature hormone. PIT targeting peak B prevents the action of the glucagon hormone. Second, vaccination with synthetic glucagon signal oligopeptides rendered immunogenic by the described methods in this disclosure, or other suitable methods known in the art, is a baseline treatment for diabetic patients.

Figure 3:
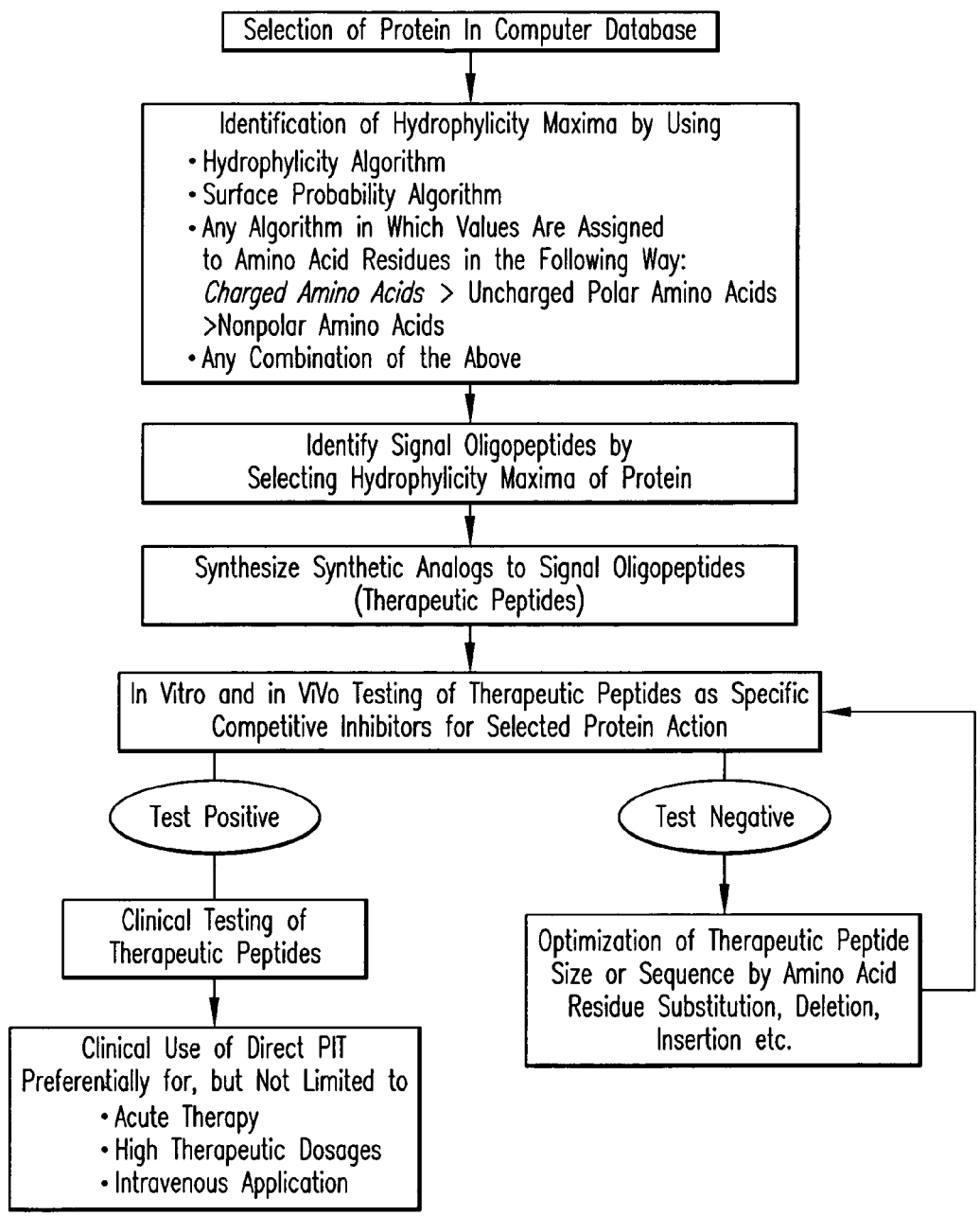

FIG. 3 shows the steps taken in order to use the are of maximum hydrophilicity of the protein sequence (signal oligopeptide) to develop synthetic analogs to the signal oligopeptide for use as competitive inhibitors.

Use of Signal Oligopeptide Sequences in Indirect Peptide Interception Therapy (IPIT)

Today vaccines are essentially limited to prophylactics and therapy of infectious diseases. Heterologous or synthetic antibody therapy, the therapeutic application of antibodies produced outside of the patient's body, can cause incalculable adverse reactions by the patient's immune system against these 'foreign' antibodies.

Peptide therapy using indirect PIT enables the extension of the preventive and therapeutic use of vaccines to all areas of medicine. The great advantage of oligopeptide vaccines as compared to conventional vaccines, is that the entire protein is not used as a vaccine. Only synthetic analogs to one or more of the signal oligopeptides of the selected protein are used to produce the vaccine. Peptide therapy by targeting the signal oligopeptide sequence "verbs" of the disease causing protein, makes elegant use of the patient's own immune system thereby excluding adverse immunological reactions.

Indirect PIT is implemented in the following manner. Signal oligopeptides of a given protein in one species of animals are the antigenic epitopes of this protein for the immune system of another species. To block the action of a pathogenicity-mediating protein in the treatment of a human disease, the amino acid residue sequence of the oligopeptide vaccines should be homologous to the signal sequences of the same protein—but from another species of animals. Thus, a glucagon signal oligopeptide vaccine for the treatment of diabetic patients would be based on the glucagon signal sequences from rabbits, sheep, mice or other species. The aim of this residue manipulation is to create an antigenic epitope without compromising the ability of the antibodies produced to effectively block the metabolic interaction of the protein. This therapeutic approach mimics nature's way to discriminate between'self and non-self and make therapeutic use of it.

Indirect PIT is based on the therapeutic use of antibodies produced by the patient's own immune system against the signal oligopeptide sequences of proteins mediating pathogenicity for undesired metabolic action. Indirect PIT is preferentially used for preventive therapy for the treatment of chronic conditions or as adjuncts to direct PIT or other forms of acute therapy.

Figure 4:
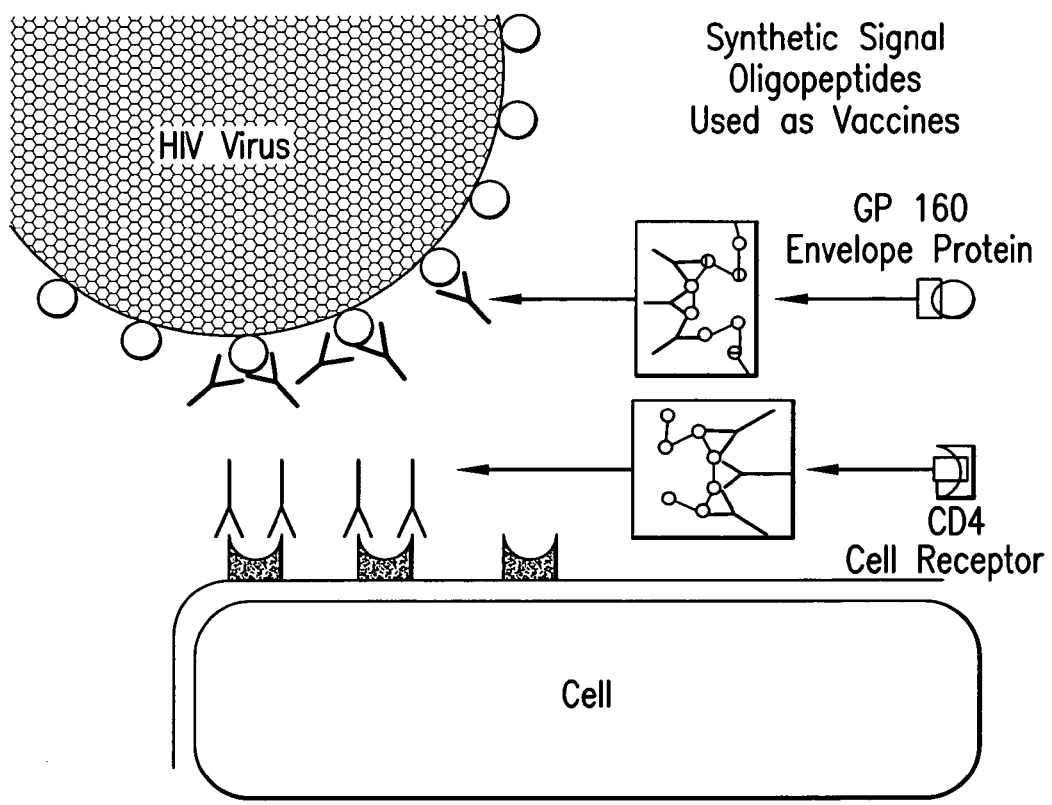
FIG. 4 shows the method of this invention used in Direct Peptide Interception Therapy (Direct PIT).

FIG. 4 shows peptide therapy in HIV infections. First, the HIV envelope protein GP 160 or the cell receptor CD4 is identified. The area of maximum electrical charge of the HIV envelope protein is then determined using the hydrophylicity blot which reveals potential signal sequences of GP 160 is used to identify the areas of maximum hydrophilicity and maximum electrical charge. Synthetic analogs to signal oligopeptides of the HIV envelope protein GP 160 or the cell receptor CD4 are then used as vaccines. The specific antibodies produced effectively inhibit the infection of cells. Other targets of HIV peptide therapy are the regulator proteins Rev and Tat with the aim to block viral replication.

Figure 5:
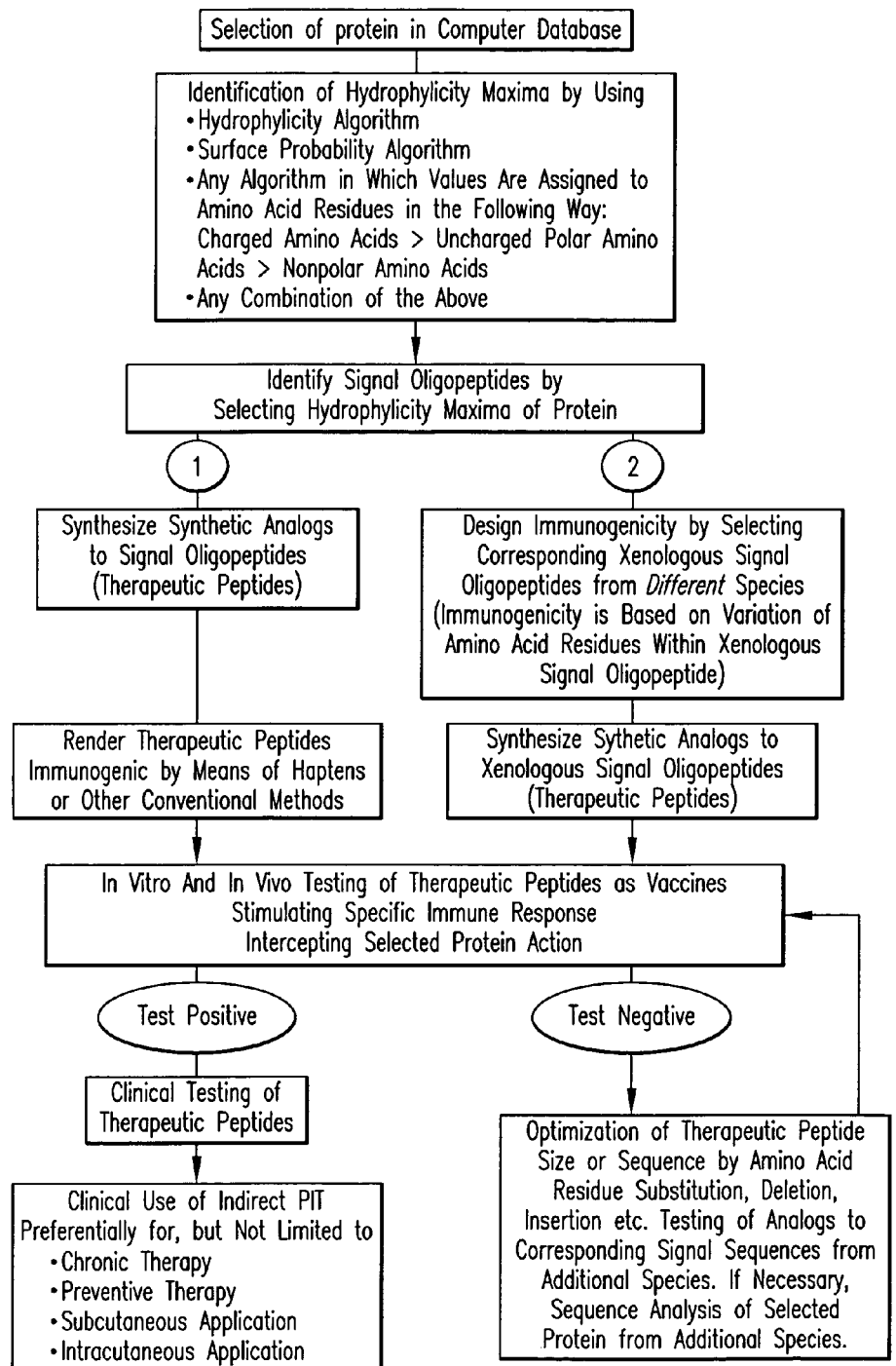
FIG. 5 shows the method of this invention used in Indirect Peptide Interception Therapy (Indirect PIT) and optimization of the therapeutic peptide size or sequence by amino acid residue substitution, deletion and/or insertions.
Figure 6:
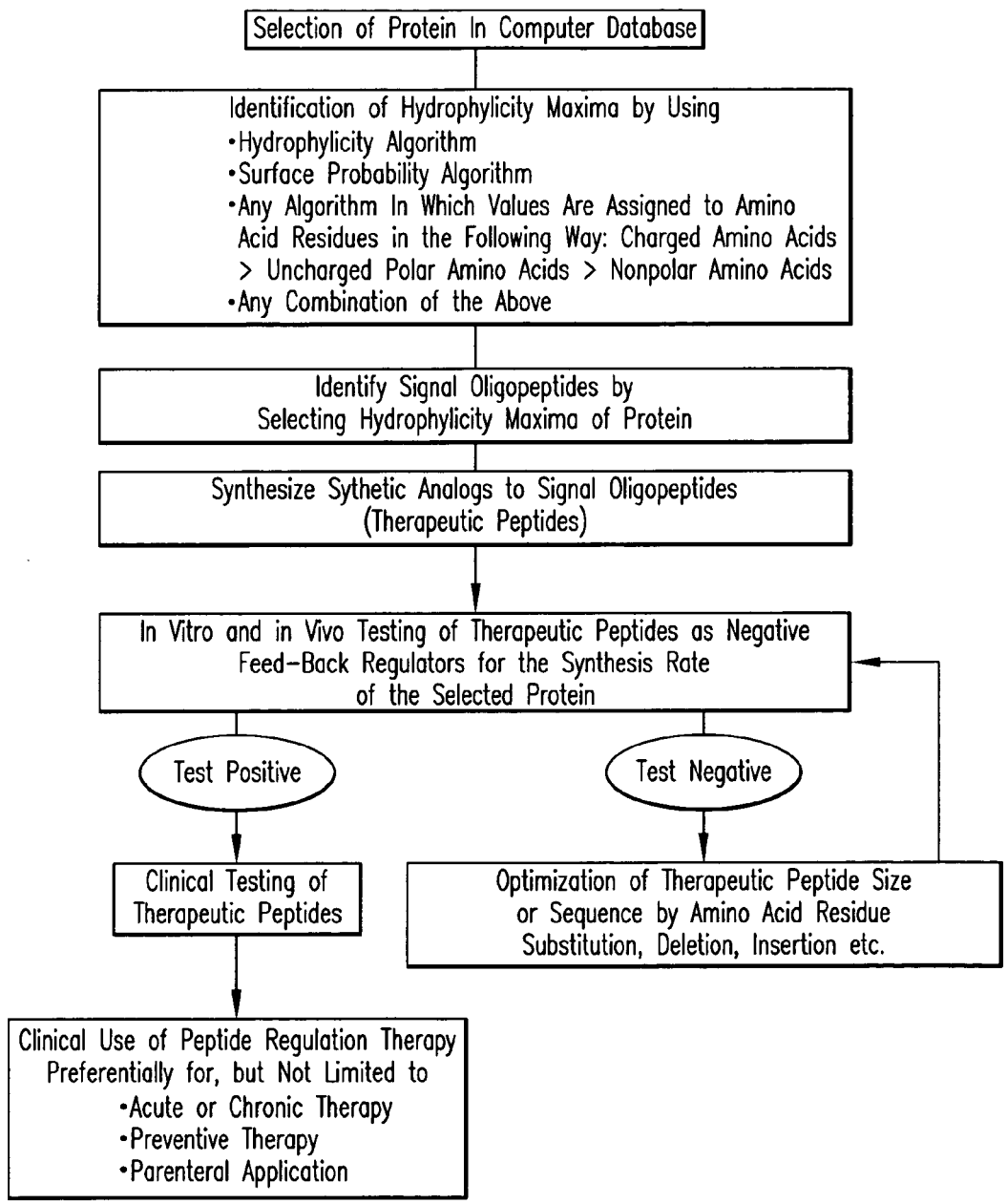
FIG. 6 shows the method of this invention used in Peptide Regulation Therapy (PRT) including the methods for identification, design, development and therapeutic use of synthetic analogs to signal oligopeptides as negative feed-back regulators for the synthesis rate of selected proteins.
Figure 7:
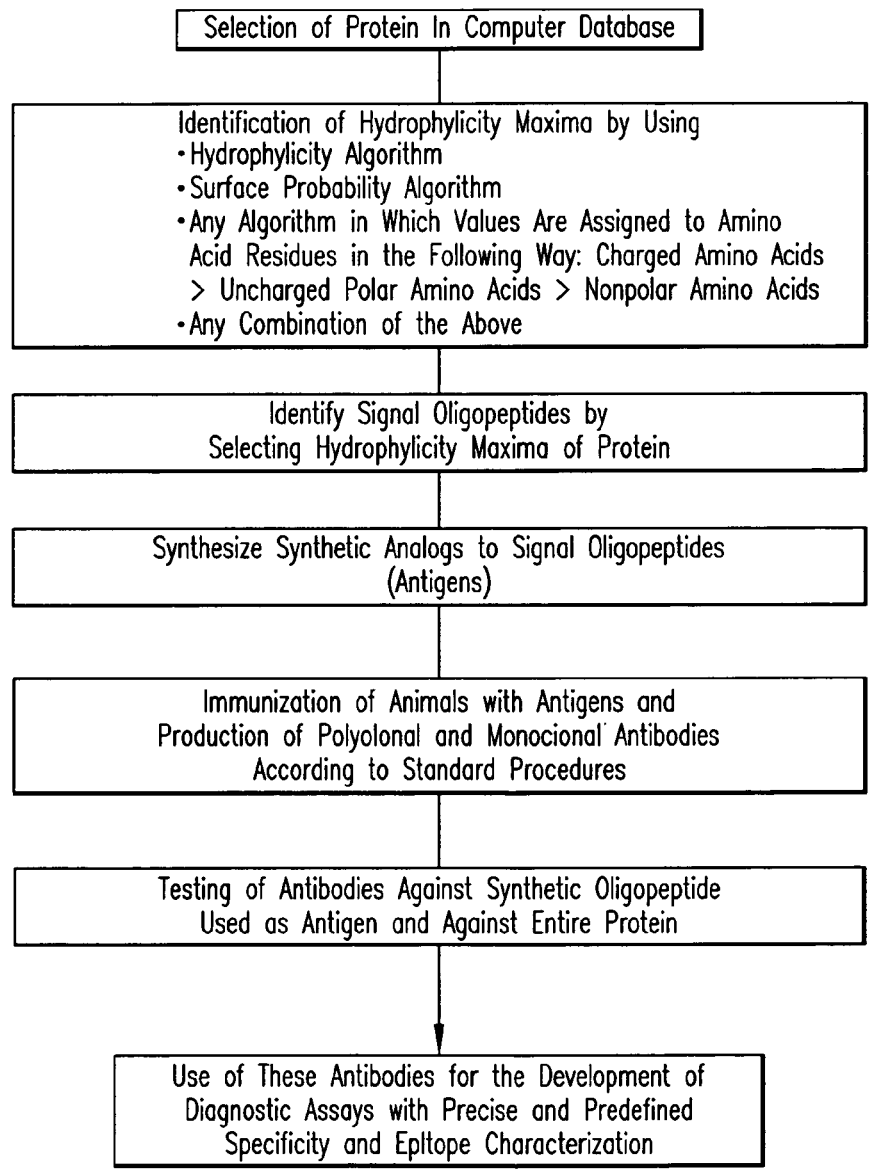
FIG. 7 shows the method of the present invention used in the development of In-Vitro Diagnostic Assays.

FIG. 5 shows the principles of Indirect Peptide Interception Therapy (Indirect PIT) including the methods for identification, design, development and therapeutic use of synthetic analogs to signal oligopeptides in Peptide Interception Therapy as vaccines to stimulate a specific immune response with the aim to decrease or block selected protein actions.

Enhancement of Immunogenic Response in Indirect Peptide Therapy

The protein code is a key for individual development within a species as well as for the evolutionary diversification of species. The effectiveness of signal oligopeptides to mediate specific biological messages were the ultimate criterion for the evolutionary advantage of a protein and, thus, for the evolutionary survival of the gene encoding for it. Genetic mutations leading to the substitution of one or more amino acid residues within a signal oligopeptide sequence were an economic and therefore frequent mechanism to modulate and differentiate protein action and thereby promoting evolutionary diversification.

The signal oligopeptides of a given protein are identical with its potential antigenicity determining regions (antigenic epitopes). Furthermore, the primary mechanism determining antigenicity between different individuals and different species are amino acid residue substitutions, omissions and other residue variations within the signal oligopeptide sequence(s) of a protein.

As shown in FIG. 5, the designer of therapeutic compounds for indirect PIT makes use of the evolutionary chain. The further apart two species of animals are in the evolutionary chain, the more: amino acid residue mutations occurred, including mutations in the signal oligopeptide sequences. Therefore, the further an animal species is from humans in the evolutionary chain, the more antigenic is the therapeutic peptide derived from that animal. A titration of the therapeutic efficiency of indirect PIT is possible. Indirect PIT therapy with synthetic analogs to glucagon signal oligopeptides from a fish species is more effective than those from a mammalian species in blocking human glucagon action.

Therefore, an evolutionary comparison method is used, wherein one or more species of animals in an evolutionary chain are selected to produce different vaccine oligopeptides to the same disease causing protein. It is desired that each vaccine oligopeptide from the different species of animals produce a different immunogenic response in vaccinated humans. Thereafter, the vaccine oligopeptide that produced the desired immunogenic response in humans is selected for use in humans.

The protein code provides the basis for the immunological differentiation between humans and animal species. Substitutions, omissions, and other variations of one or more amino acid residues within the signal sequence of the protein enable an organism to differentiate between 'self' and 'non-self'. Thus, the protein code comprises the basic language of immunology.

Antigenicity required for effective indirect PIT therapy can also be stimulated in conventional ways, e.g. by omitting one or more amino acid residues at the N-terminal end of any given sequence (start of sequence), by omitting one or more amino acid residues at the C-terminal end of any given sequence (end of terminal), by omitting one or more amino acid residues at the N-terminal and the C-terminal end of any given sequence, by substituting one or more of the amino acid residues within any given sequence without consideration of charge and polarity of the substitution residue, by substituting one or more of the amino acid residues within any given sequences with amino acid residues with similar charge and/or polarity, by omitting one or more amino acid residues within any given sequence, by coupling the therapeutic peptides to defined haptens or other immunogenic compounds enhancing 'non-self recognition, or a combination of two or more of the mentioned methods.

Use of Signal Oligopeptide Sequences in Peptide Regulation Therapy (PRT)

A third therapeutic mechanism using synthetic analogs of signal oligopeptides is as feedback regulators for protein synthesis. Peptide Regulation Therapy (PRT) makes therapeutic use of synthetic analogs of signal oligopeptide sequences to decrease the synthesis rate of an undesired protein via feedback mechanisms. The synthesis rate of many proteins is determined by the amount of protein end-product available. The signal sequences of pathogenicity mediating proteins can be used to decrease the synthesis of this protein via direct or indirect feedback mechanisms.

FIG. 6 shows the method of Peptide Regulation Therapy (PRT) including the methods for identification, design, development and therapeutic use of synthetic analogs to signal oligopeptides in Peptide Regulation Therapy as negative feedback regulators for the synthesis rate of selected proteins. Again, the area of maximum hydrophilicity of the protein sequence is determined using one of the following methods; hydrophilicity algorithm such as that described by Hobbs, Surface probability algorithm, any algorithm which assigns values to amino acid residues, higher charged amino acids receiving greater value over uncharged polar amino acid residues, over non-polar amino acids, or any combination of the above-mentioned methods.

Once the protein sequence's oligopeptide is identified, synthetic analogs are produced to match the sequence of the oligopeptide. If the synthetic analogs are not effective as feedback regulators, the analogs are optimized to produce the desired effect using peptide size alteration by amino acid residue substitution, deletion, insertion, or any combination thereof Use of Signal Oligopeptide Sequences for Development of In Vitro Diagnostics Kits Polyclonal or monoclonal antibodies for a protein can be manufactured by first identifying the antigen. Synthetic analogs to one or more signal sequences of a proteins are used as antigens. These signal sequences are determined from a data base by making use of algorithms for hydrophylicity or surface probability. For clinical diagnostics the signal sequence of the protein should preferentially be chosen from a database of human proteins.

To optimize specificity of the antigen the signal oligopeptide should be at least a tetrapeptide or preferentially longer oligopeptides. Polyclonal or monoclonal antibodies are then raised according to established methods using adjuvants or other haptens. The same synthetic signal oligopeptide analogs used as antigens can be used to test the specificity of the antibodies. FIG. 7 shows the steps involved in the method of using Signal Oligopeptides sequences in in-vitro diagnostic assays.

Use of Signal Oligopeptide Sequences in Therapeutic Applications of Peptide Therapy Infectious diseases. The most immediate application of peptide therapy is the prevention and treatment of infectious diseases. Every stage of any type of infectious disease is controlled by proteins which mediate adhesion, invasion and other mechanisms of pathogenicity. Effective therapeutic interception of biological signals within these pathogenicity-mediating proteins must lead to the control of the infection itself. As discussed above, for diseases mediated by xenologous proteins (infectious diseases) a signal sequence is chosen from xenologous protein (toxin) as basis for the vaccine in humans. The vaccines are then used for the prevention and treatment of the infectious disease.

Neoplastic Diseases. Another area with immediate applications for peptide therapy is the treatment of neoplastic diseases. Invasive growth and metastatic spread of any type of cancer is mediated by certain proteins and their signal sequences. Synthetic analogs to the signal sequences of these proteins should be developed as an effective therapy for different forms of cancer in their early stage as well as their invasive and metastatic stages.

Metabolic disorders. A novel therapeutic area for peptide therapy is the treatment of metabolic disorders. The potential of peptide therapy is exemplified here for the treatment of diabetes and hypertension, which are described in detail in the Examples below.

1. Therefore, synthetic analogs to human signal oligopeptide sequences are used for;

a. as therapeutic agents for direct competitive inhibition of selected protein interaction, b. as therapeutic agents in feedback regulation with aim to decrease the synthesis rate of the selected protein, c. as therapeutic agents in combination with haptens or other conventional immunogens or adjuvents as vaccines stimulating a specific immune response which blocks or decreases the action of the selected protein, and d. as antigens to produce antibodies against the selected human protein for invitro diagnostic purposes.

2. Synthetic analogs to protein signal sequences from other species are used;

a. as therapeutic agents (vaccines) in the prevention and treatment of human diseases, stimulating a specific immune response which blocks or decreases the action of the selected protein in the human body.

b. As therapeutic agents according to sections 1a and 1b above in the treatment of diseases in the respective animal species.

c. As antigens to produce antibodies against the selected protein for in vitro diagnostic purposes in the respective animal species.

Using the method of the invention as described above aids in the identification of potential therapeutic peptides in minutes; in vitro screening of potential peptides is a matter of weeks; and animal studies should provide first in vivo results within a few months.

EXAMPLE NO. 1

Conventional diabetic therapy aims at an increased availability of insulin. Peptide therapy allows a novel and alternative approach by inhibiting the action of glucagon, the insulin antagonist. Amino acid sequence selection and therapeutic design of peptide vaccines for Indirect Peptide Interception Therapy, exemplified for the development of glucagon vaccines in clinical therapy of diabetes mellitus is described here.

Figure 8A:
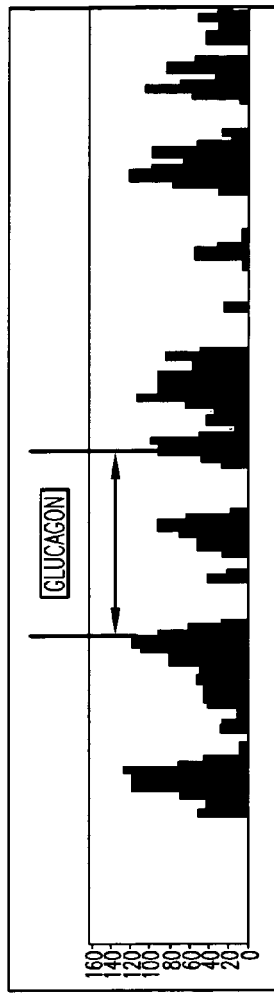
FIG. 8A shows the first two method steps.
Figure 8B:
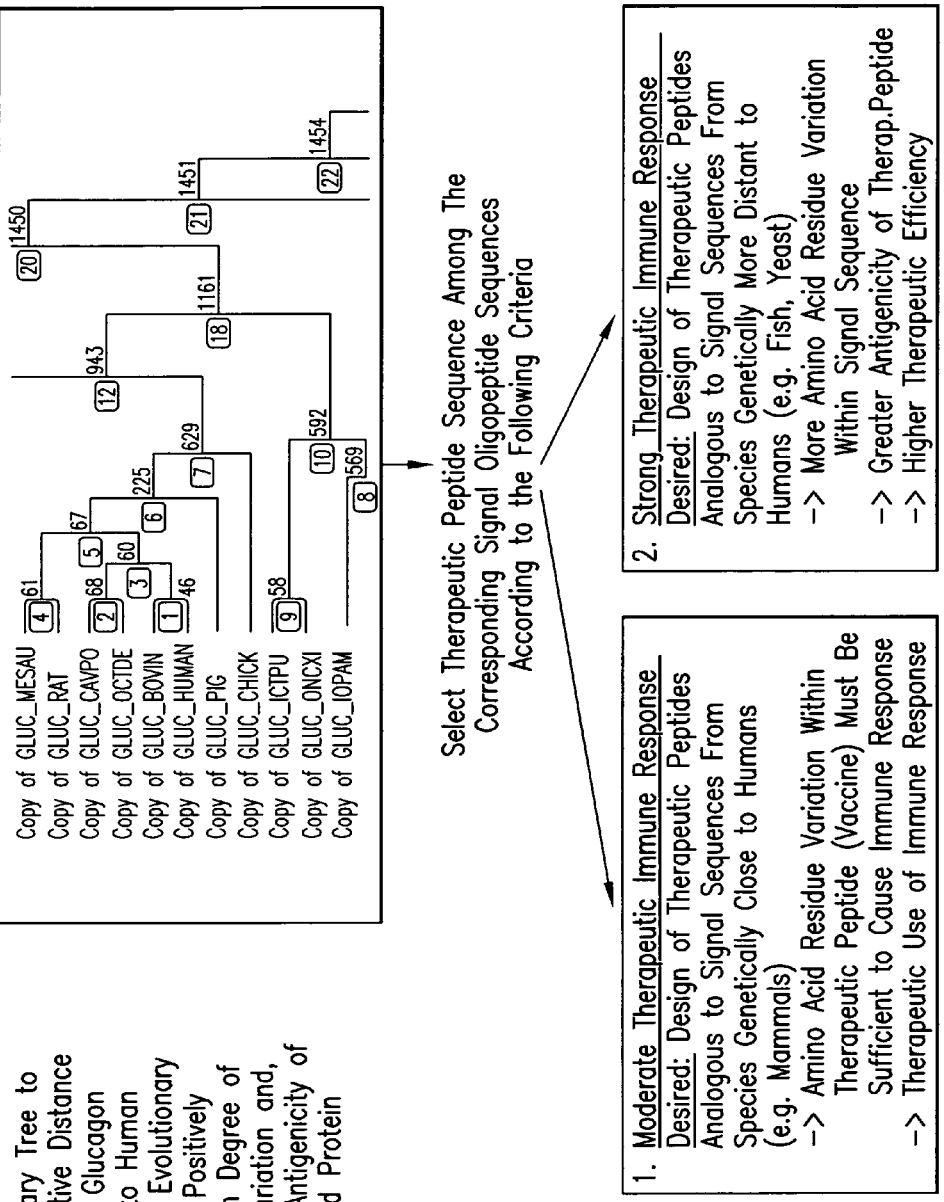
FIG. 8B shows subsequent method steps.

The inhibition of glucagon is accomplished by using the therapeutic peptides analogous to the glucagon signal sequence for direct competitive inhibition or as a vaccine (FIGS. 2 and 8). First, the signal oligopeptide is identified from a human Glucagon Precursor sequence. Using the available data for Glucagon Precursor sequences in different species, a corresponding signal oligopeptide is identified to the human oligopeptide. Using the evolutionary tree, the relative distance of the available Glucagon Sequence to the human sequence is determined. The evolutionary distance is positively correlated with degree of amino acid variation and therefore, with the antigenicity of the selected protein.

The therapeutic peptide sequence is selected among the corresponding sequences according to the following criteria. If a moderate therapeutic immune response is desired, then the therapeutic signal sequence is preferably derived from species that are genetically close to humans (e.g. mammals). Amino acid residue variation within the therapeutic peptide (vaccine) is sufficient to cause immune response in humans. If a strong therapeutic response is desired, then the therapeutic peptides are designed from species that are genetically more distant to humans (e.g. Fish, Yeast). The more distant the species from humans, the more amino acid residue variation within the signal sequence, the greater the anitgenicity of therapeutic peptide, and the higher the therapeutic efficiency.

EXAMPLE NO. 2

The specific sequences described in this application as Sequence ID Nos. 1-360 were selected using the method of the invention in order to provide specific treatments for common human diseases. The sequences so described are the signal oligopeptides characterized by a region of maximum hydrophilicity within the key protein known to mediate the indicated diseases.

For the prevention and treatment of atherosclerosis and cardioascular diseases, Therapeutic peptides from Apolipoprotein(a) (Sequence ID No.s 288 to 295). These peptides prevent the attachment of the most pathogenic lipoprotein fraction inside the artery walls, thereby preventing the formation of atherosclerotic plaques and cardiovascular diseases. Therapeutic peptides from apolioprotein(a) also competitivley detach lipoprotein(a) molecules from their binding sites inside the artery wall deposits, release them from the artery plaques and lead to the natural reversal of athereosclerosis and cardiovascular disease.

The therapeutic effect is achieved by direct application of the peptides as well as by using these peptides as vaccines and having the resulting antibodies block the binding sites. Therapeutic peptides from Famesyl Synthetase (Sequence ID Nos. 1 to 41) and therapeutic peptides from Hydroxy-Methyl-Glutaryl Coenzyme A Reductase (Sequence ID No.s 42-95). These peptides attenuate two key enzymes of cholesterol synthesis, and are therapeutically used in patients with high cholesterol levels.

EXAMPLE NO. 3

The renin angiotensin system and particularly the angiotensin-converting enzyme (ACE) are a continuous focus of antihypertensive drug development. Renin, angiotensin I and II as well as ACE are also promising targets for peptide therapy. Therapeutic use of synthetic analogs to the signal sequences of any of these proteins will lead to decreased blood pressure. Since in most cases hypertension is a chronic condition the therapeutic use of renin, angiotensin or ACE signal peptide vaccines is a preferable method of treatment.

EXAMPLE NO. 4

For the acute treatment of myocardial infarction; therapeutic peptides from Plasminogen Activator Inhibitor (PAI-1) (Sequence ID Nos. 173 to 194) and Plasminogen Activator Inhibitor 2 (PAI-2) (Sequence ID Nos. 195-214) are used to block the physiological effect of plasminogen activator inhibitor, enhance plasminogen activation and thereby promote fibrinolysis. The preferred therapeutic application of the peptides in this case is the intravenous injection of the peptides.

EXAMPLE NO. 5

The following proteins' signal sequences are derived from the method of this invention and are used for diagnostic as well as therapeutic purposes as described above.

Farnesyl Synthetase: Sequence Id Nos. 1-41
Hydroxy-Methyl-Glutaryl Coenzyme A Reductase: Sequence Id Nos. 42-163
Gonadoliberin Precursor Sequence Id Nos. 164-172
Plasminogen Activator Inhibitor 1 Sequence Id Nos. 173-194
Plasminogen Activator Inhibitor 2 Sequence Id Nos. 195-238
Herpes Virus 1 (HSV 1) Glycoprotein B Sequence Id Nos. 239-244
Herpes Virus 2 (HSV 23, 2H) Glycoprotein B Sequence Id Nos. 245-251
Treponema Pallidum Membrane Protein (TMPA) Sequence Id Nos. 252-262
Islet Amyloid Polypeptide Sequence Id Nos. 263-268
Collagenase (Fibroblast MMP 1) Sequence Id Nos. 269-280
Schistosoma, Elastase Precursor Sequence Id Nos. 281-284
Schistosomin Sequence Id Nos. 285-287
Apolipoprotein (a) Human Sequence Id Nos. 288-289
Apolipoprotein (a) Rhesus Sequence Id Nos. 290-295
Hepatitis Delta Antigen Sequence Id Nos. 296-298
Rev Protein HIV, SIV, VILV, OMVVS Sequence Id Nos. 299-348

Corticotropin Releasing Factor Binding Protein Sequence Id Nos. 349-360

EXAMPLE NO. 6

Cholesterol Measurement in Hep G2 Cells Exposed to HMG CoA Reductase Peptides:

A. Selection of therapeutic oligopeptides for these experiments
  i. The peptides were selected according to the method described herein. In brief, 6 oligopeptides corresponding to the hydrophilic amino acid maxima of human hydroxy-methyl-glutaryl-CoA-reductase were selected according to the maximum hydrophilicity determining algorithm described herein. The following sequences were selected.
    I. N-SQDEVREN-C (SEQ ID NO:42)
    II. N-ELSRESREGR-C (SEQ ID NO:44)
    III. N-RVLEEEENK-C (SEQ ID NO:46)
    IV. N-QKCDSVEE-C (SEQ ID NO:56)
    V. N-EETGINRERKVE-C (SEQ ID NO:60)
    VI. N-EPEIELPREPRPNEE-C (SEQ ID NO:64)
B. Materials and methods
  i. Hep G2 cells were seeded into six-well dishes at 30,0000 cells/well in MEM-supplemented media with 10% FBS. Cells were grown to near confluency and exposed to
    I. media alone
    II. Mevastatin 5ΦMol (Cholestrol-lowering Statin drug) and,
    III. HMG CoA Reductase peptides at 1, 10 and 100 ΦMol.
  ii. All treatments were carried out in triplicate. After 24 hrs the media was removed and saved.
  iii. The cells were washed with 1 ml of PBS and combined with the media. The cells were harvested with 1 ml of 0.1 N NaOH.
  iv. Samples, both media and cells, were saponified with 0.5 ml 50% KOH, 3 ml ethanol, separately at 80EC for 2 hrs.
  v. After cooling, the samples were extracted twice with petroleum ether and washed with NaOH.
  vi. The samples were the dried under nitrogen and suspended in 200 Φl ethanol.
  vii. 50 Φl of this suspension was used for determination of cholesterol. Cholesterol was determined in the samples and standards using colorimetric assay (Sigma Kit).
  viii. Protein was determined by Lowry's method and the results were expressed as Φgm cholesterol/mg protein.
C. Results
  i. The following results were obtained:

| Peptide | Treatment | Cholesterol Content | | Total Cholesterol | Cholesterol Lowering in |
| | | Cell | Media | (Φ gm/mg protein) | % of Control |
|---|---|---|---|---|---|
| | Control | 152.1 ± 39.0 | 66.5 ± 6.5 | 218.6 ± 35.0 | — |
| | Mevastatin 5 ΦM | 124.4 ± 4.4 | 57.5 ± 5.2 | 182.0 ± 7.0 | 18.0 |
| 1 (SEQ ID NO:42) | 1 ΦM | 92.5 ± 4.7 | 65.2 ± 4.0 | 158.7 ± 5.6 | 28.0 |
| | 10 ΦM | 88.6 ± 1.6 | 60.6 ± 0.5 | 149.1 ± 2.0 | 30.0 |
| | 100 ΦM | 94.0 ± 4.0 | 61.1 ± 2.4 | 155.3 ± 6.4 | 30.0 |
| 2 (SEQ ID NO:44) | 1 ΦM | 94.0 ± 8.3 | 64.3 ± 4.2 | 158.3 ± 6.3 | 29.0 |
| | 10 ΦM | 85.0 ± 8.4 | 63.7 ± 9.5 | 148.6 ± 11.8 | 33.0 |
| | 100 ΦM | 86.0 ± 4.7 | 59.0 ± 6.0 | 146.9 ± 8.8 | 34.0 |
| 3 (SEQ ID NO:46) | 1 ΦM | 137.3 ± 4.5 | 64.0 ± 2.7 | 201.3 ± 3.3 | 10.0 |
| | 10 ΦM | 135.0 ± 4.5 | 65.5 ± 4.7 | 200.7 ± 9.0 | 10.0 |
| | 100 ΦM | 135.0 ± 7.0 | 65.5 ± 1.4 | 200.5 ± 5.4 | 10.0 |
| | Control | 151.0 ± 7.8 | 50.8 ± 2.5 | 202.0 ± 5.3 | — |
| | Mevastatin 5 ΦM | 125.0 ± 4.6 | 37.5 ± 3.0 | 162.6 ± 7.6 | 19.0 |
| 4 (SEQ ID NO:56) | 1 ΦM | 134.7 ± 3.2 | 50.4 ± 2.5 | 184.3 ± 5.5 | 8.0 |
| | 10 ΦM | 126.1 ± 4.2 | 49.0 ± 1.0 | 175.2 ± 3.8 | 10.0 |
| | 100 ΦM | 127.7 ± 9.3 | 53.8 ± 0.5 | 181.7 ± 9.3 | 9.0 |
| 5 (SEQ ID NO:60) | 1 ΦM | 140.7 ± 8.6 | 56.8 ± 1.0 | 197.0 ± 9.2 | 1.5 |
| | 10 ΦM | 149.0 ± 4.4 | 50.7 ± 1.0 | 200.0 ± 5.0 | 0.0 |
| | 100 ΦM | 161.7 ± 23.5 | 48.0 ± 1.6 | 210.0 ± 25.0 | 0.0 |
| 6 (SEQ ID NO:64) | 1 ΦM | 144.3 ± 7.5 | 47.4 ± 0.5 | 192.0 ± 8.0 | 4.0 |
| | 10 ΦM | 136.0 ± 12.2 | 48.0 ± 3.4 | 184.0 ± 8.4 | 8.0 |
| | 100 ΦM | 132.0 ± 4.4 | 50.4 ± 1.0 | 182.4 ± 4.8 | 9.0 |

What is claimed is:

1. A method of preparing a peptide suitable for direct interception therapy in lowering cholesterol in cells comprising the steps of:
   a. identifying an amino acid sequence within the sequence of humam hydroxyl-methyl-glutaryl-CoA reductase (HMG CoA), wherein the amino acid sequence represents the maximum cationic or anionic electrical charge within the HMG CoA and is selected from the group consisting of SEQ ID NO: 42, 44, 46, 56, 60 and 64;
   b. synthesizing a peptide of the amino acid sequence identified in step a;
   c. recovering the peptide of step b, wherein the synthesized peptide functions as a a direct competitive inhibitor to reduce metabolic interaction of the HMG CoA, and wherein the synthesized peptide functions as a feed-back regulator to reduce the synthesis rate of the HMG CoA.

* * * * *